(12) United States Patent
Yahata

(10) Patent No.: US 11,942,216 B2
(45) Date of Patent: Mar. 26, 2024

(54) METHOD FOR CONTROLLING ROBOT, ROBOT, AND NON-TRANSITORY COMPUTER-READABLE RECORDING MEDIUM STORING PROGRAM

(71) Applicant: Panasonic Intellectual Property Management Co., Ltd., Osaka (JP)

(72) Inventor: Hiroshi Yahata, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 18/155,806

(22) Filed: Jan. 18, 2023

(65) Prior Publication Data
US 2023/0294294 A1    Sep. 21, 2023

Related U.S. Application Data

(63) Continuation of application No. PCT/JP2021/044440, filed on Dec. 3, 2021.

(30) Foreign Application Priority Data

Dec. 10, 2020 (JP) ................. 2020-205321
May 21, 2021 (JP) ................. 2021-086327

(51) Int. Cl.
*B25J 9/00* (2006.01)
*A63H 11/00* (2006.01)
(Continued)

(52) U.S. Cl.
CPC ............. *G16H 40/63* (2018.01); *A63H 11/00* (2013.01); *B25J 9/0003* (2013.01);
(Continued)

(58) Field of Classification Search
CPC ........ B25J 11/0005; B25J 9/0003; G05D 1/12
See application file for complete search history.

(56) References Cited

U.S. PATENT DOCUMENTS 9,526,420 B2    12/2016   Fish
2013/0123068 A1    5/2013   Sultan
(Continued)

FOREIGN PATENT DOCUMENTS

JP    2005-186234    7/2005
JP    2009-061547    3/2009
(Continued)

OTHER PUBLICATIONS

Decision to grant dated Apr. 26, 2022 issued in Japanese patent application No. 2022-508920 along with corresponding English translation.

(Continued)

*Primary Examiner* — Dalena Tran
(74) *Attorney, Agent, or Firm* — GREENBLUM & BERNSTEIN, P.L.C.

(57) ABSTRACT

A control method of a robot according to an aspect of the present disclosure includes receiving from an external computer information that instructs the robot to encourage a user to exercise; sensing a user's current position; moving the robot into a predetermined area that includes the user's current position; causing the robot to perform a gesture to encourage the user to exercise; monitoring behavior of the user; and performing driving of the robot along with exercise of the user, based on a result of the monitoring.

19 Claims, 14 Drawing Sheets

| TYPES OF ACCESS RIGHTS | | LEVEL TO BE PERMITTED (DESCRIBE ONLY THOSE OTHER THAN "0: NOT PERMITTED") |
|---|---|---|
| TASK | INDUCING TO EXERCISE | 1: ONLY LIGHT EXERCISE PERMITTED<br>2: ALL PERMITTED |
| | CONVERSATION | 1: PERMITTED |
| SENSOR | CAMERA IMAGE | 1: ONLY STILL IMAGES PERMITTED<br>2: UP TO LOW-QUALITY MOVING IMAGES PERMITTED<br>3: ALL PERMITTED |
| | RANGING SENSOR | 1: PERMITTED |
| | INFRARED SENSOR | 1: PERMITTED |
| | MICROPHONE SOUND | 1: PERMITTED |
| | TACTILE SENSOR | 1: ONLY PARTIALLY PERMITTED<br>2: ALL PERMITTED |
| | AIR TEMPERATURE/HUMIDITY/ BAROMETRIC PRESSURE SENSOR | 1: PERMITTED |
| | POSITION SENSOR | 1: PERMITTED |
| MOTOR ABILITY | ABILITY TO CHANGE FACIAL EXPRESSIONS | 1: PERMITTED |
| | ABILITY TO VOCALIZE | 1: PERMITTED |
| | ABILITY TO CHANGE POSTURE | 1: ONLY HEAD PERMITTED<br>2: ALL PERMITTED |
| | ABILITY TO MOVE | 1: PERMITTED TO MOVE AT LOW SPEED ONLY WITHIN PERMITTED HOUSE<br>2: PERMITTED TO MOVE AT LOW SPEED TO INSIDE/OUTSIDE PERMITTED HOUSE<br>3: PERMITTED TO MOVE AT HIGH SPEED TO INSIDE/OUTSIDE OF PERMITTED HOUSE<br>4: ALL PERMITTED |

(51) Int. Cl.
  *B25J 11/00* (2006.01)
  *G05D 1/00* (2006.01)
  *G16H 40/63* (2018.01)

(52) U.S. Cl.
  CPC ............ *B25J 11/0005* (2013.01); *G05D 1/12* (2013.01); *A63H 2200/00* (2013.01)

(56) References Cited

U.S. PATENT DOCUMENTS

| | | | |
|---|---|---|---|
| 2014/0278220 A1* | 9/2014 | Yuen | A61B 5/681 |
| | | | 702/150 |
| 2015/0173631 A1* | 6/2015 | Richards | A61B 5/7282 |
| | | | 600/479 |
| 2016/0005320 A1* | 1/2016 | deCharms | G09B 19/00 |
| | | | 434/236 |
| 2016/0071096 A1 | 3/2016 | Rosca | |
| 2016/0112822 A1* | 4/2016 | Giral | H04L 41/0823 |
| | | | 455/414.1 |
| 2016/0328994 A1 | 11/2016 | Nagaishi et al. | |
| 2017/0209053 A1* | 7/2017 | Pantelopoulos | A61B 5/7264 |
| 2017/0357256 A1 | 12/2017 | Mizutani | |
| 2018/0292827 A1 | 10/2018 | Artes et al. | |
| 2019/0038133 A1 | 2/2019 | Tran | |
| 2019/0077021 A1 | 3/2019 | Hayashi | |
| 2019/0138019 A1 | 5/2019 | Hayashi | |
| 2019/0147721 A1* | 5/2019 | Avitan | G06F 1/3209 |
| | | | 340/573.1 |
| 2020/0406468 A1 | 12/2020 | Stoianovici et al. | |
| 2021/0283516 A1 | 9/2021 | Hayashi | |

FOREIGN PATENT DOCUMENTS

| | | |
|---|---|---|
| JP | 2010-140119 | 6/2010 |
| JP | 2010-246676 | 11/2010 |
| JP | 2013-20587 | 1/2013 |
| JP | 2014-085975 A | 5/2014 |
| JP | 2016-038776 | 3/2016 |
| JP | 2016-209233 | 12/2016 |
| JP | 2018-536950 A | 12/2018 |
| JP | 2019-107461 | 7/2019 |
| WO | 2017/199662 | 11/2017 |
| WO | 2019/198310 | 10/2019 |
| WO | 2020/122236 | 6/2020 |

OTHER PUBLICATIONS

International Search Report of PCT application No. PCT/JP2021/025720 dated Sep. 21, 2021.
International Search Report of PCT application No. PCT/JP2021/044440 dated Feb. 22, 2022.
Traficante, R. M. (2004). Computer-based interventions, health behavior change, and ethics (Order No. 3133900). Available from ProQuest Dissertations and Theses Professional. (305048423). Retrieved from https://dialog.proquest.com/professional/docview/305048423?accountid=131444 (Year:2004).

* cited by examiner

FIG. 5

| | TYPES OF ACCESS RIGHTS | LEVEL TO BE PERMITTED (DESCRIBE ONLY THOSE OTHER THAN '0: NOT PERMITTED') |
|---|---|---|
| TASK | INDUCING TO EXERCISE | 1: ONLY LIGHT EXERCISE PERMITTED<br>2: ALL PERMITTED |
| | CONVERSATION | 1: PERMITTED |
| SENSOR | CAMERA IMAGE | 1: ONLY STILL IMAGES PERMITTED<br>2: UP TO LOW-QUALITY MOVING IMAGES PERMITTED<br>3: ALL PERMITTED |
| | RANGING SENSOR | 1: PERMITTED |
| | INFRARED SENSOR | 1: PERMITTED |
| | MICROPHONE SOUND | 1: PERMITTED |
| | TACTILE SENSOR | 1: ONLY PARTIALLY PERMITTED<br>2: ALL PERMITTED |
| | AIR TEMPERATURE/HUMIDITY/BAROMETRIC PRESSURE SENSOR | 1: PERMITTED |
| | POSITION SENSOR | 1: PERMITTED |
| MOTOR ABILITY | ABILITY TO CHANGE FACIAL EXPRESSIONS | 1: PERMITTED |
| | ABILITY TO VOCALIZE | 1: PERMITTED |
| | ABILITY TO CHANGE POSTURE | 1: ONLY HEAD PERMITTED<br>2: ALL PERMITTED |
| | ABILITY TO MOVE | 1: PERMITTED TO MOVE AT LOW SPEED ONLY WITHIN PERMITTED HOUSE<br>2: PERMITTED TO MOVE AT LOW SPEED TO INSIDE/OUTSIDE PERMITTED HOUSE<br>3: PERMITTED TO MOVE AT HIGH SPEED TO INSIDE/OUTSIDE OF PERMITTED HOUSE<br>4: ALL PERMITTED |

FIG. 6

| NECESSARY URGENCY DEGREE | REQUESTS TO BE PERMITTED |
|---|---|
| HIGH | REQUESTS WITH URGENCY CONCERNING LIFE, HEALTH, DANGER, OR RISK OF PROPERTY LOSS ARE PROCESSED. OTHERWISE, REQUEST IS SUSPENDED OR REJECTED. |
| MEDIUM | IN ADDITION TO REQUESTS WHOSE NECESSARY URGENCY DEGREE IS CLASSIFIED AS "HIGH", REQUESTS NOTIFYING USERS OF IMPORTANT INFORMATION IN DAILY LIFE (NOTIFICATION OF NEXT SCHEDULE OR OF STATE AT RISK OF SIGNIFICANT LOSS (SUCH AS LEAVING GAS OVEN ON)) ARE PROCESSED. OTHERWISE, REQUEST IS SUSPENDED OR REJECTED. |
| LOW | ALL REQUESTS ARE PROCESSED. |

FIG. 10

| TIME ZONE | USER'S STATE | UPDATING OF NECESSARY URGENCY DEGREE BY ROBOT | NECESSARY URGENCY DEGREE |
|---|---|---|---|
| 8:00–10:00 | TALKING | USING SENSOR, ROBOT DETECTS THAT USER IS TALKING WITH ANOTHER PERSON, AND SETS NECESSARY URGENCY DEGREE TO "MEDIUM". FURTHERMORE, BASED ON RESULT OF SENTIMENT ANALYSIS OF USER, ROBOT MAY CHANGE NECESSARY URGENCY DEGREE. | MEDIUM |
| 10:00–12:00 | WORKING | USING SENSOR, ROBOT DETECTS THAT USER IS OPERATING PERSONAL COMPUTER, AND MAINTAINS THE NECESSARY URGENCY DEGREE AT "MEDIUM". | MEDIUM |
| 12:00–13:00 | HAVING MEAL | USING SENSOR, ROBOT DETECTS THAT USER IS HAVING MEAL, AND UPDATES NECESSARY URGENCY DEGREE TO "LOW". | LOW |
| 13:00–15:00 | ON PHONE / IN MEETING | USING SENSOR, ROBOT DETECTS THAT USER IS TALKING OR IN MEETING VIA MOBILE PHONE OR PERSONAL COMPUTER, AND UPDATES NECESSARY URGENCY DEGREE TO "MEDIUM". | MEDIUM |
| 15:00–16:00 | EXERCISING | USING SENSOR, ROBOT DETECTS THAT USER IS EXERCISING, AND MAINTAINS NECESSARY URGENCY DEGREE AT "MEDIUM". FURTHERMORE, WHEN THERE IS PERIODIC CHANGE IN USER'S SKIN COLOR OR WHEN HEART RATE IS LOW, ROBOT MAY UPDATE NECESSARY URGENCY DEGREE TO "LOW". | MEDIUM |
| 16:00–20:00 | RELAXING | USING SENSOR, ROBOT DETECTS THAT USER IS IN RELAXING STATE, AND UPDATES NECESSARY URGENCY DEGREE TO "LOW". | LOW |

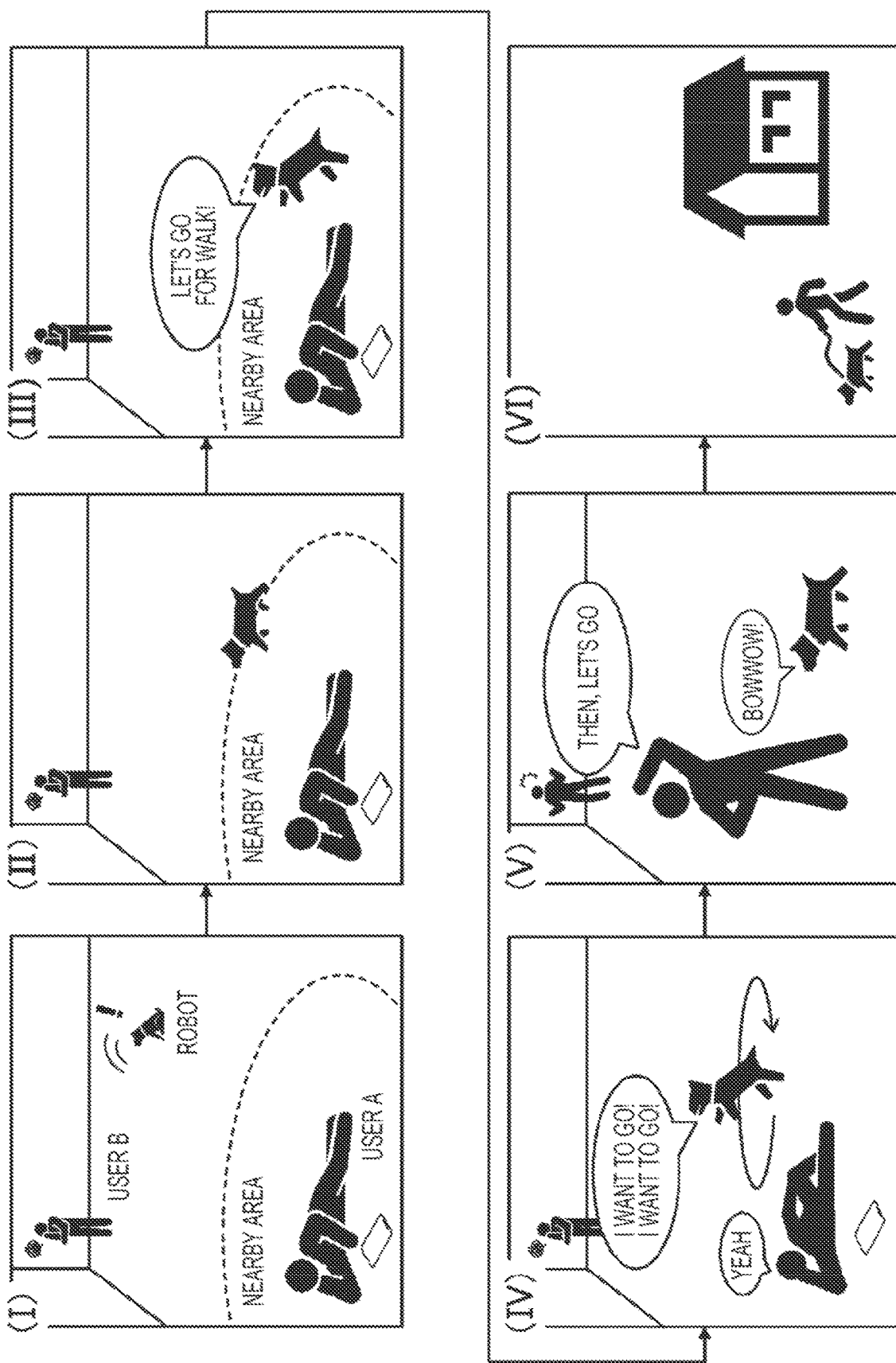

METHOD FOR CONTROLLING ROBOT, ROBOT, AND NON-TRANSITORY COMPUTER-READABLE RECORDING MEDIUM STORING PROGRAM

BACKGROUND

1. Technical Field

The present disclosure relates to a control method for a robot, a robot, and a non-transitory computer-readable recording medium storing a program.

2. Description of the Related Art

Japanese Patent No. 6495486 (referred to as PTL 1) discloses a method, as an autonomous robot that considers physical conditions of a user, of measuring body temperatures of the user and determining the user's condition based on a cycle of the measured body temperatures, and a method of changing an amount of operation of the robot when a basal temperature cycle reaches a predetermined timing.

SUMMARY

Further improvement of robot functions is desired in the conventional robot technology.

In one general aspect, the techniques disclosed here feature a method for controlling a robot, comprising: receiving, from a first computer that is external to the robot, instruction information that instructs the robot to encourage a user to exercise; detecting a current position of the user through an optical sensor included in the robot; controlling at least one pair of wheels or legs of the robot to cause the robot to move into a predetermined area including the current position of the user; controlling at least one actuator included in the robot to cause the robot to perform a gesture for encouraging the user to exercise; monitoring behavior of the user through the optical sensor or a microphone included in the robot; and controlling, based on a result of the monitoring, the at least one actuator included in the robot to drive the robot along with exercise of the user.

According to the control method of the robot according to the one aspect of the present disclosure, it is possible, through the robot, to give the user a strong motivation to exercise.

It should be noted that general or specific embodiments may be implemented as a system, a method, an integrated circuit, a computer program, a storage medium, or any selective combination thereof."

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a table illustrating an example of setting information of an access right about a robot;

FIG. 6 is a table illustrating an example of level of urgency degree for determining whether or not it is possible to execute a requested task;

FIG. 10 is a table illustrating an example of setting of necessary urgency degree;

FIG. 14 is a diagram illustrating an example of processing performed by the robot according to the embodiment of the present disclosure.

DETAILED DESCRIPTIONS

Figure 1:
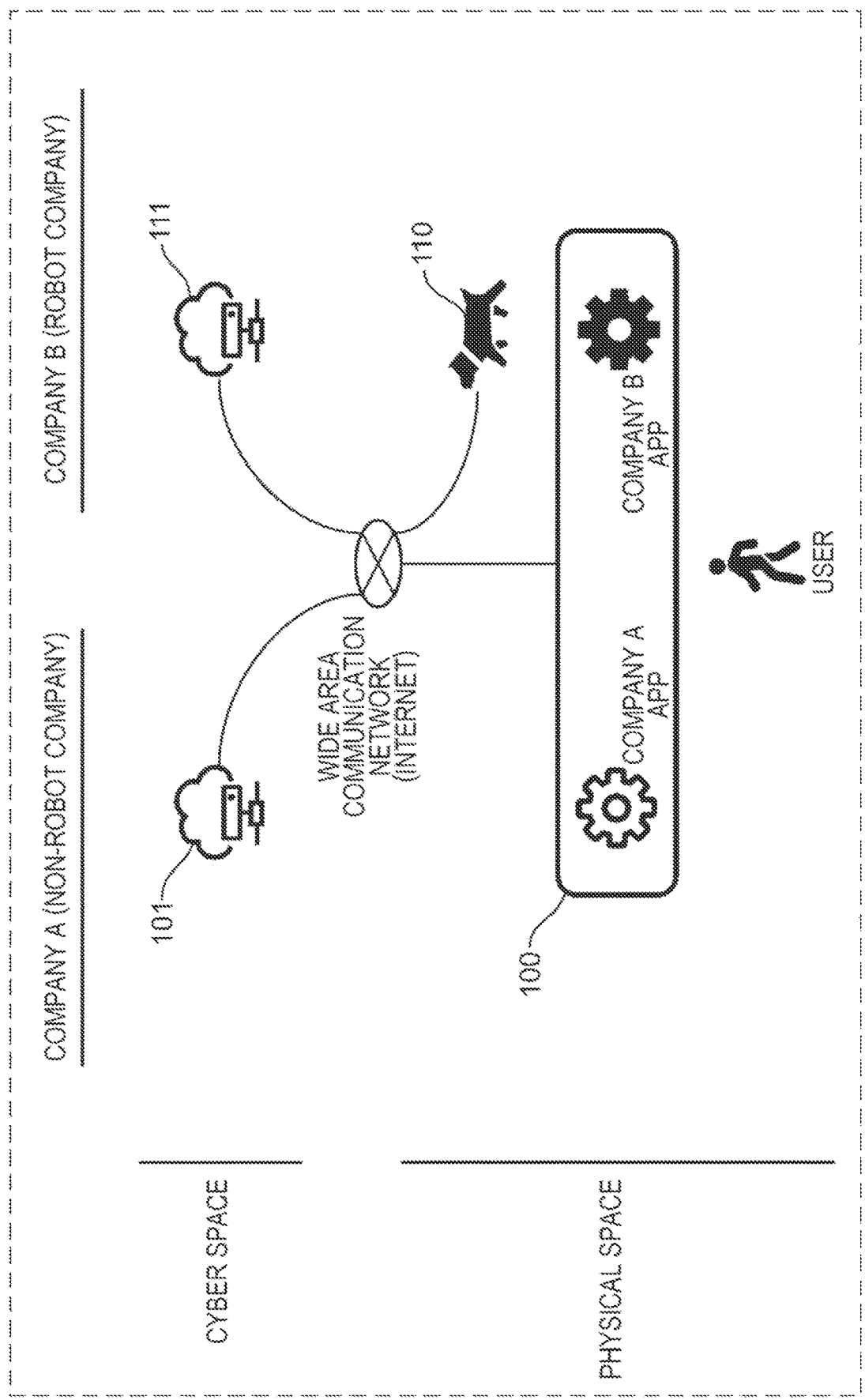
FIG. 1 is a block diagram illustrating an example of an overall configuration of an information system according to an embodiment of the present disclosure.

Underlying Knowledge Forming Basis of the Present Disclosure

Our daily lives have been increasingly digitalized. For example, many people have smartphones that are information communication terminals dedicated for private use. Users have come to install in smartphones and to use various applications (an application is hereinafter referred to as an app), such as an app for performing their health management, an app for family budget management, a social communication app for supporting real-time communications with acquaintances, and a news app that curates news in the world in accordance with interests of an individual.

On the other hand, but gradually, a movable device (hereinafter referred to as a robot) capable of autonomously performing various operations or tasks has been put into practice. Those robots are robots that assemble or adjust parts in factories, robots that perform accurate and quick sorting at physical distribution bases, robots that fulfill specific tasks in light of surrounding circumstances, or the like. These robots also include robots that perform work in cooperation with humans or that perform a specific task on behalf of humans.

The present disclosure proposes a technique for assisting users so that the users can lead a healthy, happy, comfortable, secured, safe, enjoyable, and/or clean life, by a smartphone and a robot, which is a mobile device, operating in cooperation with each other, the smartphone being an information processing device capable of performing various information processing, and the mobile device capable of executing tasks that handle various operations and objects.

If biological activity information of a user is collected and it is confirmed from the collected biological activity information that the user lacks exercise, it is possible to urge the user to exercise by presenting a message inducing the user to exercise through the user's smartphone. A message prompting the users to change their behavior in this manner is called a nudge.

However, it is not easy to cause the users who do not have an exercise habit to change their behavior. Simply presenting the nudge to the users is not sufficient and a stronger motivation than the nudge is needed.

In PTL 1 described above, there is disclosed a technique for estimating, from owner's body temperatures, timing of consideration when a robot should give consideration to an owner, in view of an owner's menstrual cycle and for causing the robot, which usually behaves on its own, to behave considerately, such as staring at the owner at the estimated consideration timing, thereby enhancing sympathy of the owner for the robot.

As such, since PTL 1 is the technique of enhancing the sympathy between the owner and the robot, it is not possible to give users a strong motivation for exercise.

The present disclosure has been made to solve such a problem and aims to provide a technique that can give users a strong motivation for exercise.

A control method of a robot according to one aspect of the present disclosure includes: receiving, from a computer that is external to the robot, instruction information that instructs the robot to encourage a user to exercise; detecting a current position of the user through an optical sensor mounted in the robot; controlling at least one pair of wheels or legs of the robot to cause the robot to move into a predetermined area including the current position of the user; controlling at least one actuator included in the robot to cause the robot to perform a gesture for encouraging the user to exercise; monitoring behavior of the user through the optical sensor or a microphone mounted in the robot; and controlling, based on a result of the monitoring, the at least one actuator included in the robot to drive the robot along with exercise of the user.

In this method, the robot comes close to the user and performs the gesture to encourage the user to exercise. Therefore, the robot is capable of encouraging the user to exercise more actively than a case in which a message encouraging the user to exercise through text or sound is simply presented. As a result, it is possible to give the user a strong motivation to exercise.

Note that an "actuator" in the present disclosure may be an actuator for actuating wheels or legs or an actuator for actuating other member as a body action of the robot.

For example, the driving of the robot along with the exercise of the user may be performed if the behavior of the user includes an affirmative response to the gesture of the robot or expression of an intention to take exercise.

For example, the exercise of the user may include the user moving by walking or running, and the driving of the robot along with the exercise of the user may include controlling the at least one pair of wheels or legs to cause the robot to move accompanying the user who is moving.

This makes it possible for the robot capable of accompanying the user to encourage the user to walk or run. Therefore, the user can find an inviting message, such as "Let's take a walk together", from the action of the robot that encourages exercise. As a result, it is possible to give the user the strong motivation to exercise through the robot.

For example, the driving of the robot along with the exercise of the user may further include controlling the at least one pair of wheels or legs to cause the robot to encourage the user to start moving while leading the user in a direction away from the predetermined area.

This makes it possible to realize an action to invite the user to exercise, thus smoothly shifting to start of exercise after the action to encourage the user to exercise.

For example, the gesture for encouraging the user to exercise may be a gesture to convey to the user an intention of the robot to take a walk.

This makes it possible to induce user's motivation for exercise by giving the user an altruistic motivation to "go along with the robot that desires to take a walk", even when the user himself or herself is less motivated to take a walk.

For example, the monitoring of the behavior of the user may include detecting a change in a posture of the user through the optical sensor.

For example, the monitoring of the behavior of the user may include acquiring voice information spoken by the user through the microphone and performing voice recognition on the voice information.

For example, the gesture for encouraging the user to exercise may be repeatedly performed until a response from the user to the gesture is detected.

For example, the control method may further include: before the robot starts to move into the predetermined area, detecting a remaining amount of a battery mounted in the robot; and starting movement of the robot, if the remaining amount of the battery is larger than an amount of power required for driving the robot.

For example, the above control method may further include: monitoring the behavior of the user who is exercising through the optical sensor or the microphone; and transmitting to the computer an end notice indicating the user has finished exercising, after determining that the user has finished exercising.

For example, the above control method may further include: transmitting, to the computer, necessary urgency degree information that indicates an urgency degree which is required for the computer to cause the robot to fulfill an instruction, in which the instruction information may be transmitted from the computer to the robot if an urgency degree that should encourage the user to exercise meets the urgency degree which is required.

For example, the computer may be a server or an information communication terminal that is communicable with the robot via a network.

For example, the computer may transmit the instruction information to the robot according to request information received from another computer via a network, the request information being information that requests the robot to encourage the user to exercise, and the other computer may transmit a message for encouraging the user to exercise, and may transmit the request information to the computer if it is determined that an amount of exercise taken by the user does not satisfy a predetermined target amount after transmission of the message.

For example, the detecting of the current position of the user may include: determining whether or not the user who is identified by the instruction information and should be encouraged to exercise is detected around the robot; and acquiring information on the current position of the user in a three-dimensional space, if it is determined that the user is detected.

For example, the gesture for encouraging the user to exercise may be a gesture involving an action of the robot to encourage the user.

For example, the gesture may be performed by driving the at least one pair of wheels or legs of the robot.

For example, the exercise may be walking or running, and the driving of the robot along with the exercise of the user may include controlling the at least one pair of wheels or legs to induce the robot to take the user out of home, and controlling the at least one pair of wheels or legs to cause the robot to move accompanying the user who is walking or running out of home.

A robot according to another aspect of the present disclosure includes: a main body; at least one pair of wheels or legs; at least one actuator; at least one of an optical sensor or a microphone; a processor; and a memory in which a program for causing the processor to execute the above control method is stored.

A non-transitory computer-readable recording medium storing a program according to still another aspect of the present disclosure causes a processor mounted in a robot to perform the above control method.

Note that the present disclosure can also realize a program for causing a computer to execute respective characteristic configurations in the control method of the robot and the information providing method which are used here, or a system operated by this program. In addition, it is needless to say that such a computer program can be distributed through a non-transitory computer readable storage medium such as a CD-ROM or the like, or through a communication network such as Internet or the like.

Note that any of embodiments described below illustrates a specific example of the present disclosure. Numeric values, shapes, components, steps, or a sequence of steps depicted in the following embodiments are an example, and do not limit the present disclosure. In addition, among components in the following embodiments, components not described in independent claims that represent the highest-level concept are described as arbitrary components. In addition, in all of the embodiments, contents of the respective embodiments can be combined.

Embodiments

It is expected that in our society, Internet will further spread and various types of sensors will be familiar. As a result, it is expected that our society will be in a state where information on an internal state and activities of individuals or the like as well as information on an entire city including buildings and transportation networks or the like will be digitalized and become available to computer systems. Digitalized data regarding individuals (personal information) will be safely managed as big data in a cloud server such as information banks, via communication networks, and utilized for various purposes for individuals and the society.

Such an advanced information society is called Society 5.0 in Japan. The advanced information society has an information infrastructure (cyber physical system) that highly integrates a real space (physical space), which is a material world surrounding individuals and a virtual space (cyber space) where computers cooperate with each other to perform various processes related to the physical space. The advanced information society is a society where economic growth and solution of social issues are expected.

In such an advanced information society, by analyzing communications (including acquisition and provision of information, as well as a method of expressing the information) or behaviors by an individual in various scenes of his or her daily life, and analyzing the big data including the accumulated personal information, it is possible to provide information or services necessary for that individual, in a way of communication that seems most suitable for that individual, according to the scene.

Hereinafter, given the advanced information society where such a cyber physical system works, a description is given of specific aspects that enhance health and happiness of users, with support for daily life close to individual users as a theme.

FIG. 1 is a block diagram illustrating an example of an overall configuration of an information system according to an embodiment of the present disclosure. FIG. 1 illustrates a cyber space in an upper half and a physical space in a lower half. On the left side, resources related to company A that is a non-robot provider company are lined up. A company A server 101 is in the cyber space and a company A app running on a smartphone 100 is in the physical space. The company A server 101 operates as a pair with the company A app. On the right side resources related to company B that is a robot provider are lined up. A company B server 111 is in the cyber space, and a robot 110, which is a movable device, and a company B app running on the smartphone 100 are in the physical space. The company B server 111 operates as a pair with the robot 110 and/or the company B app. In the middle of the physical space, there is a user who handles the company A app and the company B app installed on the smartphone 100, and the robot 110. The smartphone 100, the robot 110, the company A server 101, and the company B server 111 are connected by a wide area communication network such as the Internet, so that they can communicate with each other.

As illustrated in FIG. 1, the company A and the company B have contact points with users through their respective apps and robots. The company A only has the contact points via the app on the smartphone 100, which is a form of a customer contact that is often seen today. On the other hand, the company B in FIG. 1 also has the contact points via the robot 110, in addition to the contact points via the app on the smartphone 100. Companies that have contact points with users (general consumers) via the robot 110, which is an autonomous movable device, are unprecedented except for some toy manufacturers, and are expected to emerge in the future.

Note that here, although an illustration of a dog-shaped robot is used as an example of the robot 110, the robot 110 may have a form based on any other living creatures including humans or may have an inorganic and non-living form. As far as the robot 110 has autonomous motor abilities (ability to change posture and ability to move, or the like) and/or an ability to operate (ability to move other objects, such as pressing a button or lifting an object) in the physical space, the robot is not limited in its form.

In an information system which is an embodiment of the present disclosure, the robot 110, and home appliances and housing equipment operated by the robot 110, or the like which are contact points of each customer are more highly linked than ever before. It can be said that it is an information system that expands the range of improvement in the quality of its own services and provides the users with a higher value while utilizing information and capabilities held by others. The cognitive and motor abilities of robots are evolving day by day. If such a versatile robot is realized, a mechanism is to be built that allows other companies to access unique abilities held by the robot. It is believed that doing so will be a basis for creating a wide variety of value collaborations for users, non-robot companies that provide services, and robot companies that provide robots.

Figure 2:
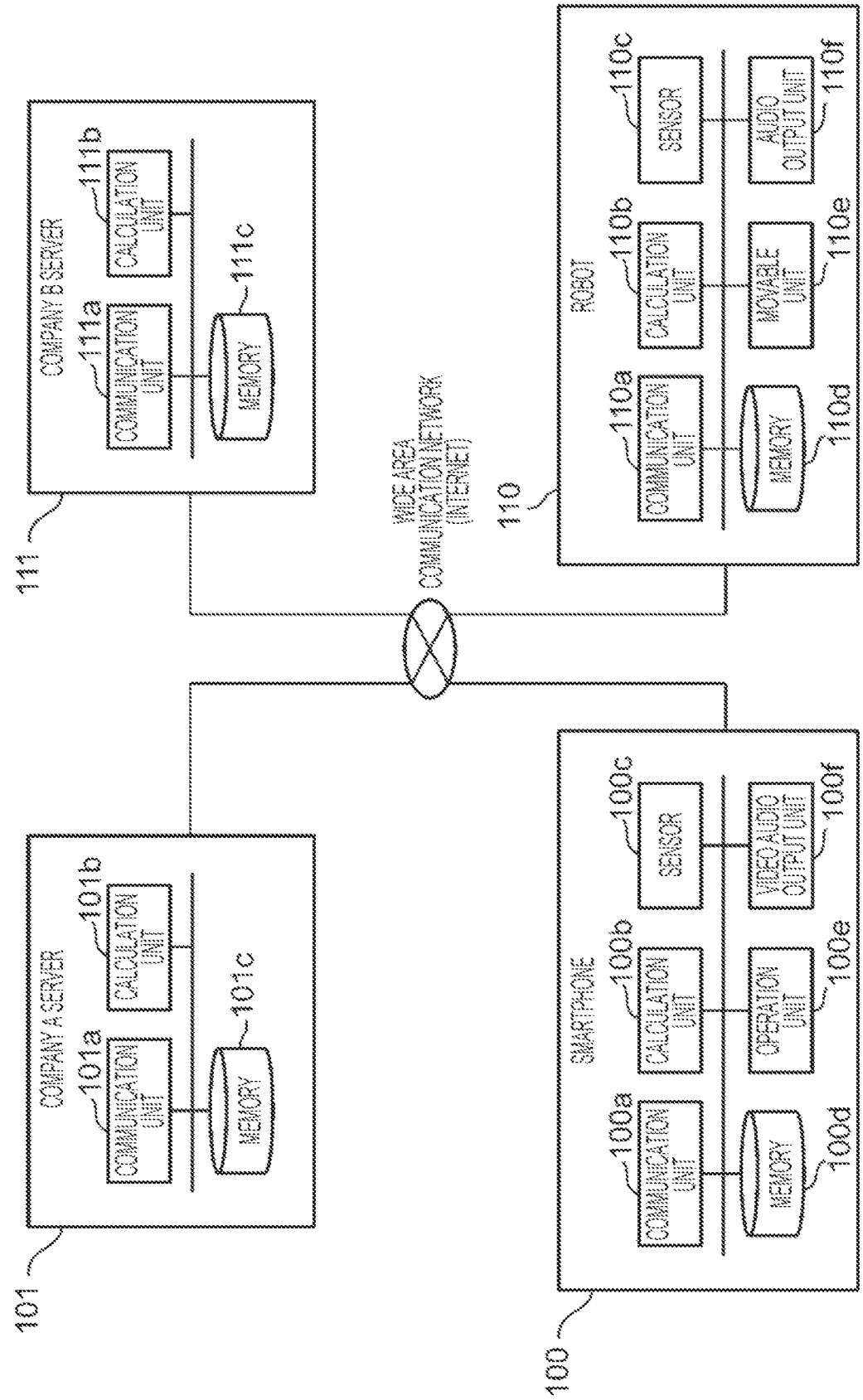
FIG. 2 is a block diagram illustrating an example of the configuration of the information system according to the embodiment of the present disclosure.

FIG. 2 is a block diagram illustrating an example of a configuration of the information system according to the embodiment of the present disclosure. The smartphone 100 includes a communication unit 100a, a calculation unit 100b, a sensor 100c, a memory 100d, an operation unit 100e, and a video audio output unit 100f. The sensor 100c is a device that acquires video information, audio information, and/or surrounding environment information. The sensor 100c includes, for example, an image sensor and a microphone.

The video audio output unit 100f is a device that outputs video and audio. The video audio output unit 100f includes, for example, a display and a speaker. The operation unit 100e is a device that receives a button press or a touch operation from the user. The operation unit 100e includes, for example, a touch panel and a button. The calculation unit 100b is a device that performs information processing such as voice recognition, voice synthesis, information search, and information drawing, that is performed in the smartphone 100. The calculation unit 100b is, for example, a central processing unit. The memory 100d holds data processed by the calculation unit 100b. The memory 100d is, for example, a semiconductor memory such as a flash memory. The communication unit 100a is a communication circuit that performs information communications with other computers on a network. When both the company A app and the company B app are installed, a program and necessary data are recorded in the memory 100d of the smartphone 100, and that program is executed by the calculation unit 100b.

The company A server 101 operates in cooperation with the company A app installed on the smartphone 100. The company A server 101 includes a communication unit 101a, a calculation unit 101b, and a memory 101c. The communication unit 101a is a communication circuit for performing information communications with the other computers on the network. The memory 101c records information related to the company A app and the user. The memory 101c is, for example, a mass storage such as a hard disk drive and a solid state drive. The calculation unit 101b performs processing of data exchanged with the outside. The calculation unit 101b is, for example, a processor such as a central processing unit.

The company B server 111 operates in cooperation with the company B app installed on the smartphone 100. The company B server 111 includes a communication unit 111a, a calculation unit 111b, and a memory 111c. The communication unit 111a is a communication circuit for performing information communications with the other computers on the network. The memory 111c records information related to the company B app, the robot 110, and the user. The memory 111c is, for example, a mass storage such as a hard disk drive and a solid-state drive. The calculation unit 111b performs processing of the data exchanged with the outside. The calculation unit 111b is, for example, a processor such as a central processing unit.

The robot 110 includes a communication unit 110a, a calculation unit 110b, a sensor 110c, a memory 110d, a movable unit 110e, and an audio output unit 110f. The sensor 110c is a device that acquires video information, audio information, and/or surrounding environment information. The sensor 110c includes, for example, an image sensor and a microphone. The audio output unit 110f is, for example, a speaker and outputs audio. The robot 110 may include an operation unit (not illustrated) that receives a button press or a touch operation from the user. The movable unit 110e is a device that controls the posture of the robot 110 under the control of the calculation unit 110b, and moves the robot itself and provides dynamic actions on other objects. The movable unit 110e is, for example, an actuator such as a motor. The calculation unit 110b performs various calculation processes that are performed in the robot 110. The calculation unit 110b is, for example, a processor such as a central processing unit. The memory 110d holds data processed by the calculation unit 110b. The memory 110d is, for example, a semiconductor memory such as a flash memory. The communication unit 110a is a communication circuit for performing information communications with the other computers on the network.

Note that although the company A server 101, the smartphone 100, the robot 110, and the company B server 111 are connected via the wide area communication network so that they can communicate with each other, they may be connected by a dedicated communication network or Near Field Communication or the like, when low-latency communications, strong security, or local paring is requested, or the like.

Providing Robot Capabilities in Health Management

Hereinafter, a description is given of an embodiment in which health management of the user is carried out more effectively by using the familiar robot 110.

Figure 3:
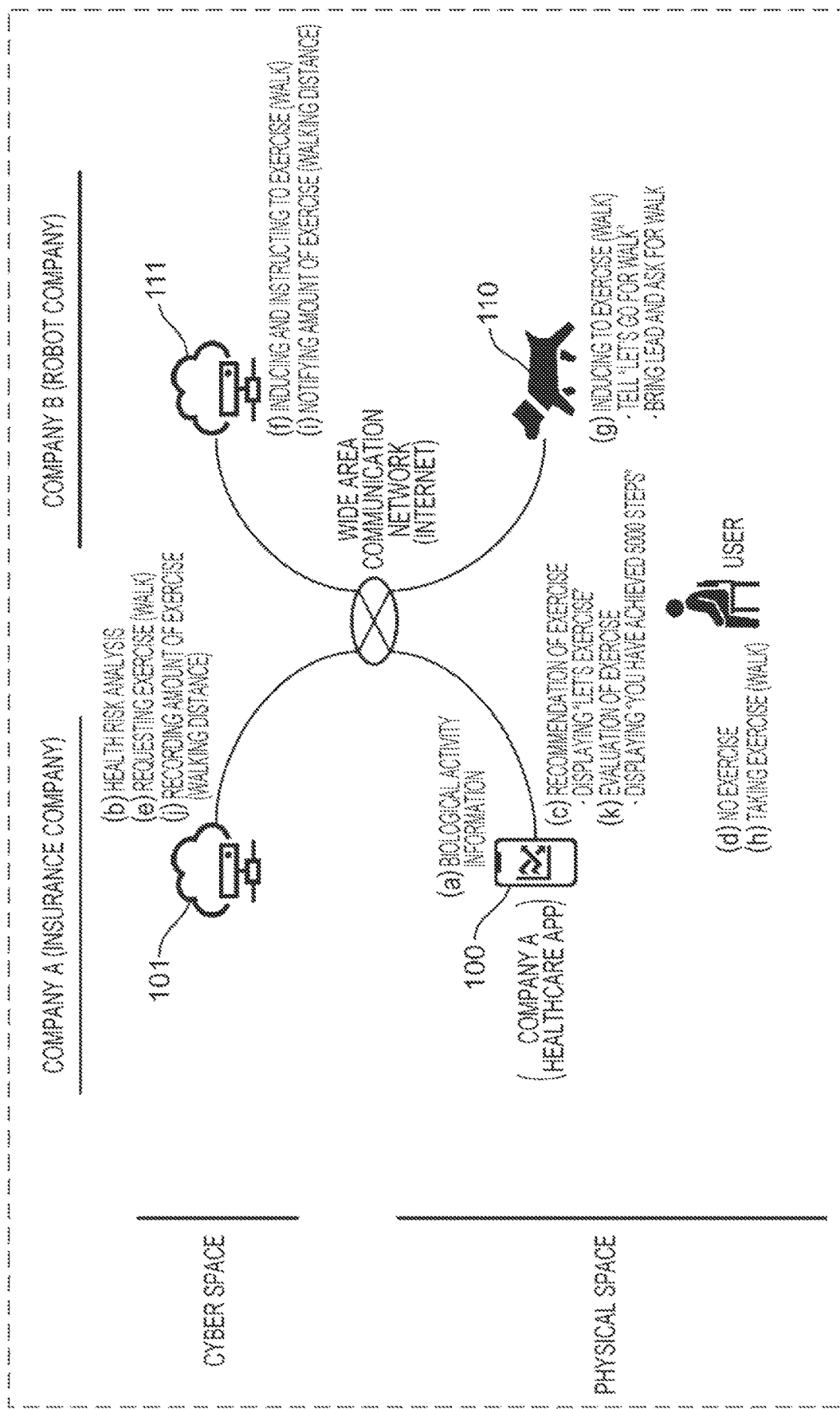
FIG. 3 is a block diagram illustrating an example of an overall configuration of an information system according to a form of one form of the present disclosure.

FIG. 3 is a block diagram illustrating an example of an overall configuration of an information system according to an embodiment of the present disclosure. In this form, the company A, which is the non-robot company, is a health insurance company with which the user has a contract. To improve health of the user, the company A, which is an insurance company, has the user install a healthcare app, which is provided by the company A, on the smartphone 100 and use the app every day. The company A healthcare app continuously collects the biological activity information of the user (heartbeat, pulse, blood pressure, body temperature, body water content, breathing, sweating amount, activity amount (consumed calories), an intake amount (calorie intake), number of steps, posture, and a type of exercise, or the like) by a wearable sensor or the like on a daily basis. The company A healthcare app records the biological activity information in the memory 100d of the smartphone 100, and, at the same time, periodically uploads the biological activity information to the company A server 101 ("(a) Biological activity information" in FIG. 3).

The biological activity information collected in this manner is strictly managed by the company A server 101 as personal information of the user. The company A server 101 periodically analyzes health risk of the user based on the biological activity information of the user ("(b) Health risk analysis" in FIG. 3). Furthermore, when it is determined that the amount of exercise taken by the user is insufficient, the company A server 101 transmits a nudge to the user in order to recommend the exercise. For example, a message "Let's exercise." causing a behavior change so that the user takes a desirable action is displayed via the company A app ("(c) Recommendation of exercise" in FIG. 3). However, generally speaking, behavior change urged by this type of approach easily fails to give a sufficient motivation and often cannot solve the user's lack of exercise ("(d) No exercise" in FIG. 3).

Conventional services provided in the information society until now (also called Society 4.0 society) have been realized for a loop of (a) to (d), which are described here. With the conventional services, the cyber space and the physical space can cooperatively work to have a continuous contact with users and promote health improvement. In the conventional services, however, the biological activity information and the services are confined only in the services of the company A, and there is no cooperation with any entity other than the company A. The conventional services are in a silo state, so to speak. It seems that even though the company A slightly changes the expressions of the message displayed on the smartphone 100, there are still many users who cannot easily change their behaviors. Therefore, the conventional services are not sufficient to be services that widely improve the health of users. In the present embodiment, the robot that is familiar to the user and has the autonomous motor abilities is used, and the autonomous motor abilities that are not held by the company A app but held by the robot are used to envision services for improving the health of the user. Forms to realize the services are described. Now, continuation of FIG. 3 is described.

If the company A server 101 determines from the periodically uploaded biological activity information that the user has not taken sufficient exercise even after the company A server 101 (one example of the second server) transmits the nudge to recommend exercise, the company A server 101 transmits request information for requesting the robot 110 to execute a task of encouraging the user to exercise (walk, for example) to the company B server 111 (one example of the first server) with which cooperation has been set in advance ("(e) Requesting exercise (walk)" in FIG. 3). More specifically, the request information is transmitted after it is determined in the company B server 111 that it is necessary to encourage the user to exercise. A description of the advance cooperation setting between the servers is given below.

When the company B server 111 that has received the request information confirms that the company A server 101 has the access right to the requested task, the company B server 111 decides to execute, suspend, or reject the request. Then, if the company B server 111 decides to execute the request, the company B server 111 outputs, to the robot 110 held by that user, instruction information that induces the user to exercise (walk) ("(f) Inducing and instructing to exercise (walk)" in FIG. 3). This instruction information includes an instruction for the robot 110 to specifically present in a form understandable by the user how the robot behaves and what the robot requests of the user. For example, in the case of the dog-shaped robot, the instruction information for inducing to exercise that is received by the robot 110 includes an instruction for the robot 110 to directly tell the user "Let's go for a walk" or to bring a lead used for a walk and ask the user to go for a walk (showing its willingness to go for a walk), or the like. Contents of these specific instructions are included in the instruction information for inducing to exercise that is transmitted from the company B server 111 to the robot 110, and the instruction is executed by the robot 110 ("(g) Inducing to exercise (walk)" in FIG. 3).

The user who is thus asked by the dog-shaped robot to exercise (walk) together may be motivated more strongly than the nudge regarding the exercise received via the smartphone 100. As a result, the user finally exercises (takes a walk) ("(h) Taking exercise (a walk)" in FIG. 3). Here, a variety of methods for inducing by the robot 110 is possible and the foregoing is merely an example thereof. For example, if the robot 110 held by the user is too small to go for a walk together, or if the robot 110 imitates a living object (for example, a frog) that is unlikely to go for a walk, an inducing method for causing the frog-shaped robot to say "I want to see the nearby river", or the like, and guiding the user on the route thereto with the frog-shaped robot resting on the user's hand can be employed.

When the task requested by the instruction information ends, the robot 110 notifies the company B server 111 of information indicating that the user took exercise (a walk) and taken exercise amount information that includes a travel distance thereof or a walking speed. The company B server 111 that has received the taken exercise amount information notifies the company A server 101 of the taken exercise amount information (for example, a walking distance) as a final result for "(e) Requesting for exercise (walk)" ("(i) Notifying the amount of exercise (walking distance)" in FIG. 3).

The company A server 101 records the taken exercise amount information ("(j) Recording the amount of exercise (walking distance)" in FIG. 3), praises the user's exercise based on the taken exercise amount information, and presents to the user an evaluation message that evaluates the user's exercise, such as "You have achieved 5000 steps" or the like, through the company A app, in order to increase the user's motivation to exercise ("(k) Evaluation of exercise" in FIG. 3).

Note that the company A app or the company A server 101 may feed back to the user the evaluation message like "(k) Evaluation of exercise" in FIG. 3, without being based on the taken exercise amount information that is obtained from the company B server 111. For example, the company A server 101 may display the evaluation message on the screen of the smartphone 100 by obtaining the biological activity information "(a) Biological activity information in FIG. 3" from a step sensor worn by the user.

It was difficult to cause the behavior change that increases the amount of exercise of the user, only by messages such as video information and audio information on the smartphone 100, which is the customer contact point of the company A. By the company A asking for a walk via the dog-shaped robot provided by the company B and the dog-shaped robot further walking together, it is possible to lower the user's psychological barrier to exercise (walk) and increase the amount of exercise of the user. Moreover, the user can expect that this will allow the user to better maintain the health.

When the robot 110 asks the user to change his/her behavior in this manner, and the robot 110 conveys its own intention or desire (wishing to go for a walk) to the user as if it were a living system, the user may want to let that living system (robot) do what it wants. This is because the user is requested to change his/her behavior based on the altruistic desire to meet the request of the robot, which is the living system with one will, rather than being requested to change his/her behavior solely based on the user's selfish desire to maintain the health. The service for maintaining the user's health disclosed here is an approach that combines the approach based on the selfish desire that can be independently realized by the company A with the altruistic desire that can only be realized through cooperation with the company B robot 110.

It can also be said that this information system is an information system in which the apps or the robot 110, which are respective customer contact points, are linked at a higher level, and improve the quality of their services while utilizing the information and the capabilities held by others, thereby providing the users with higher values. The cognitive and motor abilities of robots are evolving day by day. If such a versatile robot is realized, a mechanism is to be built that allows other companies to access unique abilities held by the robot. Doing so will be a basis for creating a wide variety of value collaborations for users, non-robot companies (company A) that provide services, and robot companies (company B) that provide robots 110.

Figure 4:
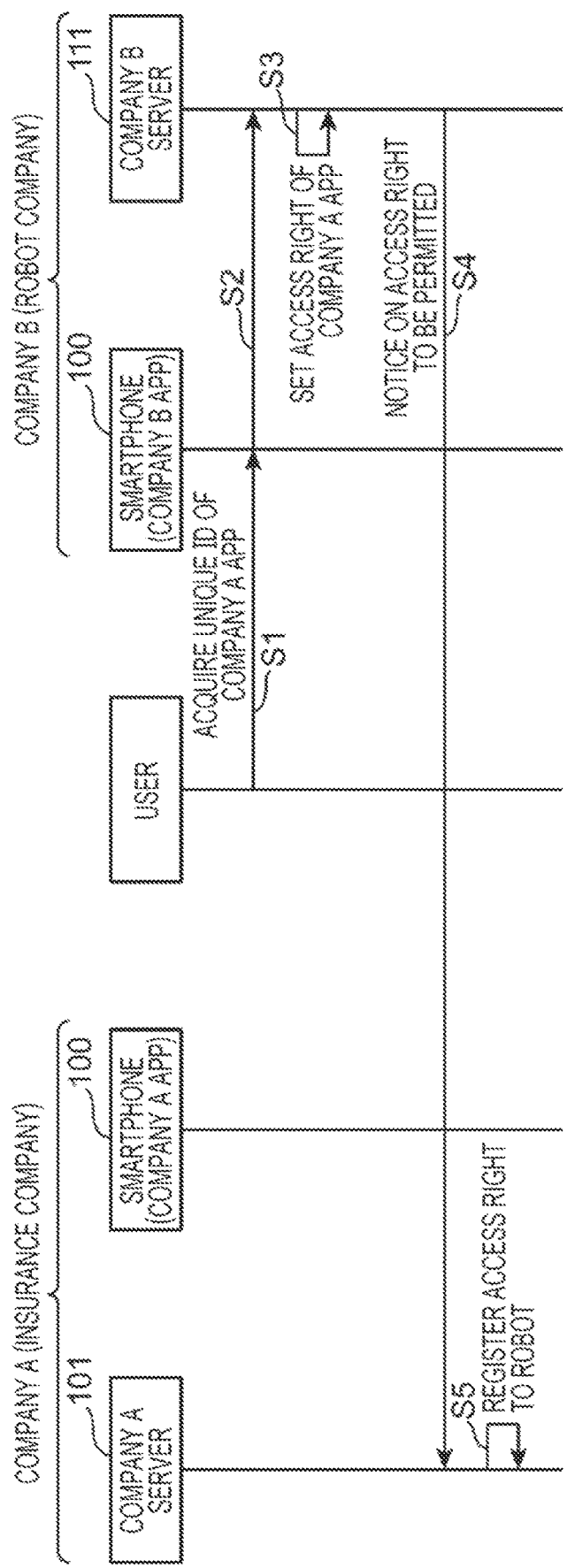
FIG. 4 is a flowchart illustrating an example of processing when a non-robot company (company A) works with a robot.

FIG. 4 is a flowchart illustrating an example of processing when the non-robot company (company A) cooperates with the robot 110. For the company A app or the company A server 101 as illustrated in FIG. 3 to access the information and the capabilities of the robot 110 operated by the company B, it is necessary to appropriately set its access right in advance. FIG. 4 illustrates an example of a process to set the access right in advance.

Using the company B app installed in the smartphone 100, the user sets the company B app to cooperate with the company A app. Specifically, based on the user's input, the company B app acquires a unique ID of the company A app used by the user (step S1). The company B app transmits a registration request for registering with the company B server 111 the acquired unique ID of the company A app together with a unique ID of the company B app (step S2). The company B server 111 that has received the registration request registers pair information of the company A app and the company B app. In this registration process, the access right is simultaneously registered, the access right indicating to what extent the company A is granted a right to access which of the unique capabilities of the robot 110 (step S3). Details of the access right is described below with reference to FIG. 5. The pair information including the robot ID of the robot 110 and the unique ID of the company B app has been registered in advance in the company B server 111. This registration is performed, for example, by the user inputting the unique ID of the robot 110 on an initial setting screen of the company B app.

The company B server 111 that has received the registration of the company A app notifies the company A server 101 of setting information on the access right for which the company A app is permitted (step S4). Specifically, the company B server 111 notifies the company A server 101 of the access right setting information, in addition to the pair information of the unique ID of the company A app and the unique ID of the company B app.

The company A server 101 registers with the memory 101c the pair information of the unique ID of the company A app and the unique ID of the company B app, and the access right setting information (step S5). When the company A app or the company A server 101 uses its unique capabilities for the robot 110 provided by the company B, the information is used to identify a target robot 110 and to determine whether or not the unique capabilities can be used.

Here, it suffices if the access right to the robot 110 provided by the company B is correctly set for the company A app or the company A server 101. The foregoing is merely an example thereof. Any registration method other than the above may be used.

FIG. 5 is a table illustrating an example of the access right setting information for the robot 110. The company A can request various tasks from the robot 110 of the company B. Furthermore, the robot 110 is provided with various sensors 110c and the motor abilities (movable unit 110e). The access rights thereto from the company A are registered in the company B server 111 as well as the company A server 101 that is the user side. Hereinafter, types of the access rights and permission levels thereof are described below. The setting of the access rights is performed by the user in step S3 of FIG. 4.

The types of the access rights are classified into "Task", "Sensor", and "Motor Ability". The "Task" is further classified into "Inducing to exercise" and "Conversation". The "Sensor" is further classified into "Camera image", "Ranging sensor", "Infrared sensor", "Microphone sound", "Tactile sensor", "Air temperature/humidity/barometric pressure sensor", and "Position sensor". The "Motor Ability" is further classified into "Ability to change facial expressions", "Ability to vocalize", "Ability to change a posture", and "Ability to move".

The "Inducing to exercise" that belongs to the "Task" is the access right indicating to what extent the non-robot company (company A) can request the robot 110 for the task of encouraging the user to exercise. The exercise mentioned here is, for example, walk, jogging, squats, push-ups, swimming, and yoga, or the like, and may be of any type. Here, for convenience of explanation, it is expressed that the access right is given when a request can be made, and that the access right is not given when a request cannot be made. The access right to "Inducing to exercise" is set in a stepwise manner as follows: from "0" without access right to "2" with the access right without limitation. For example, in response to a request for the "Inducing to exercise" task from the non-robot company (company A) whose permission level of this access right is "1", a robot operating company (company B) permits a request for light exercise that is less than or equal to predetermined exercise load, and controls the robot 110 and/or the company B server 111 within the permitted range.

0: Not permitted
   1: Only light exercise permitted
   2: All permitted

The "Conversation" that also belongs to the "Task" is the access right that indicates to which extent the non-robot company (company A) can request for talking with the user via the robot 110. The access rights to the "Conversation" can be set by selecting from the following two choices: "0" without access right or "1" with access right. For example, the robot operating company (company B) gives a permission to the request for the "Conversation" from the non-robot company (company A) whose permission level is "1", as having the access right. The robot operating company (company B) sets the microphone ("Microphone Sound" of the sensor 110c) and the speaker ("Ability to vocalize" of the Motor ability) to be accessible to the non-robot company (company A). Consequently, the non-robot company (company A) controls the robot 110 and/or the company B server 111 so that the user and the robot 110 can have a conversation. Therefore, if the access right to the "Conversation" task is also given, in conjunction therewith, the robot operating company (company B) also sets so that the non-robot company (company A) has the access right to the "Microphone sound" of the sensor 110c and the "Ability to vocalize" of the Motor ability.

0: Not permitted
   1: Permitted

As described above, the task is used to determine whether or not to execute the request when the robot company receives the request for the robot 110 to execute some task, from the non-robot company. Therefore, the access right setting information in FIG. 5 is set for each non-robot company.

Note that in the present disclosure, a series of autonomous operations for the robot 110 to perform some encouragement or perform action on the user and/or a target object (for example, a TV remote controller, a lighting switch, or a door knob) in the real space, based on a request from the non-robot company is referred to as a task.

The "Camera image" is the access right to an image sensor (for example, an RGB image sensor) included in the robot (110). This may be an image sensor that is provided in a place that is apparently perceived as eyes of the robot. The access right to the "Camera image" can be set in a stepwise manner as follows: from "0" without access right to "3" with the access right given without limitation. For example, in response to the access request from the non-robot company (company A) whose permission level is "2", the robot operating company (company B) controls the robot 110 and/or the company B server 111 to return a low-quality moving image.
  0: Not permitted
  1: Only still images permitted
  2: Up to low-quality moving images permitted
  3: All permitted The "Ranging sensor" is the access right to the sensor 110c (for example, a TOF sensor, a LIDAR, or the like) capable of measuring a distance to an object included in the robot 110. The access right to the "Ranging sensor" can be set by selecting from the following two choices: "0" without access right or "1" with access right. For example, in response to the access request from the non-robot company (company A) whose permission level is "1", the robot operating company (company B) controls the robot 110 and/or the company B server 111 to return data (for example, a depth image) acquired by the ranging sensor.
  0: Not permitted
  1: Permitted The "Infrared sensor" is the access right to a sensor included in the robot 110 and capable of measuring infrared rays. An infrared sensor is used to recognize a subject in the dark in a near-infrared region and to measure a temperature distribution of the subject in a far-infrared region. The access right to the "Infrared sensor" can be set by selecting from the following two choices: "0" without access right or "1" with access right. For example, in response to the access request from the non-robot company (company A) whose permission level is "1", the robot operating company (company B) controls the robot 110 and/or the company B server 111 to return data (for example, a thermography image) acquired by the infrared sensor.
  0: Not permitted
  1: Permitted The "Microphone sound" is the access right to the microphone included in the robot 110. The access right to the "Microphone sound" can be set by selecting from the following two choices: "0" without access right or "1" with access right. For example, in response to the access request from the non-robot company (company A) whose permission level is "1", the robot operating company (company B) controls the robot 110 and/or the company B server 111 to return audio data acquired by the microphone.
  0: Not permitted.
  1: Permitted The "Tactile sensor" is the access right to a sensor (for example, a MEMS silicon hair device sensor) included in the robot 110 and capable of measuring tactile sensation on a surface of the robot. The access right to the "Tactile sensor" can be set in a stepwise manner as follows: from "0" without access right to "2" with the access right given without limitation. For example, in response to a request from the non-robot company (company A) whose permission level is "1", the robot operating company (company B) controls the robot 110 and/or the company B server 111 to return only data on a part (for example, a head) of the robot, of data (for example, a pressure distribution image) acquired by the tactile sensor.
  0: Not permitted
  1: Only partially permitted
  2: All permitted The "Air temperature/humidity/barometric pressure sensor" is the access right to an air temperature sensor, a humidity sensor, and a barometric pressure sensor included in the robot 110. The access right to the "Air temperature/humidity/barometric pressure sensor" can be set by selecting from the following two choices: "0" without access right or "1" with access right. For example, in response to the access request from the non-robot company (company A) whose permission level is "1", the robot operating company (company B) controls the robot 110 and/or the company B server 111 to return data acquired by the air temperature sensor, the humidity sensor, and the barometric pressure sensor, respectively.
  0: Not permitted
  1: Permitted The "Position sensor" is the access right to a sensor included in the robot 110 and measuring a current position of the robot. The access right to the "Position sensor" can be set by selecting from the following two choices: "0" without access right or "1" with access right. For example, in response to the access request from the non-robot company (company A) whose permission level is "1", the robot operating company (company B) controls the robot 110 and/or the company B server 111 to return data indicating information on the robot's current position that is acquired by the position sensor.
  0: Not permitted
  1: Permitted The above is the explanation on the access rights to the sensors 110c included in the robot 110. Then, the access rights to the motor abilities the robot is provided with are described below.

The "Ability to change facial expressions" is the access right to the ability of the robot 110 to change external characteristics of a face. When the robot 110 has a section that can be apparently perceived as a face, this may be an ability to move parts making up that face or an ability to change a part color. The access right to the "Ability to change facial expressions" can be set by selecting from the following two choices: "0" without access right or "1" with access right. For example, in response to the access request from the non-robot company (company A) whose permission level is "1", the robot operating company (company B) controls the robot 110 and/or the company B server 111 to change the facial expressions according to the request for changing the facial expressions.
  0: Not permitted
  1: Permitted The "Ability to vocalize" is the access right to the audio output capability provided in the robot 110. When the robot 110 has a section that can be apparently perceived as a mouth, this may be an ability to move parts making up the mouth or an ability to output sound from a periphery of the mouth. The access right to the "Ability to vocalize" can be set by selecting from the following two choices: "0" without access right or "1" with access right. For example, in response to the access request from the non-robot company (company A) whose permission level is "1", the robot operating company (company B) controls the robot 110 and/or the company B server 111 to output the sound from the periphery of the mouth according to audio information that should be vocalized.
  0: Not permitted
  1: Permitted The "Ability to change posture" is the access right to an ability to change a posture that is included in the robot 110. This may be an ability to change angles of a plurality of joint mechanism parts in the movable unit 110e of the robot 110. However, this is not an ability to change a position of the robot 110 itself. The access right to the "Ability to change posture" can be set in a stepwise manner as follows: from "0" without access right to "2" with the access right given without limitation. For example, in response to the access request from the non-robot company (company A) whose permission level is "1", the robot operating company (company B) controls the robot 110 and/or the company B server 111 to move only the head according to the request.

0: Not permitted
1: Only head permitted
2: All permitted

The "Ability to move" is the access right to the ability to move included in the robot 110. This may be the ability to change the angles of the plurality of joint mechanism parts in the movable unit 110*e* of the robot 110. However, the "Ability to move" is an ability to change the position of the robot 110 itself. The access right to the "ability to move" can be set in a stepwise manner as follows: from "0" without access right to "4" with the access right given without limitation. For example, in response to the access request from the non-robot company (company A) whose permission level is "1", the robot operating company (company B) controls the robot 110 and/or the company B server 111 to allow the robot to move at low speed in an area permitted by the user in the user's house. For example, in response to the access request from the non-robot company (company A) whose permission level is "3", the robot operating company (company B) controls the robot 110 and/or the company B server 111 to allow the robot to move at high speed only inside and outside the area of house permitted by the user. Here, the area permitted by the user is one of conditions set by the user in advance. For example, it is possible to set in advance so that the robot cannot approach an area (for example, a bathroom) where the user's privacy may be violated.

0: Not allowed
1: Permitted to move at low speed only within the permitted house
2: Permitted to move at low speed to inside/outside the permitted house
3: Permitted to move at high speed to inside/outside the permitted house
4: All permitted FIG. 6 is a table illustrating an example of the level of urgency degree for determining whether or not the requested task can be executed. The description on FIG. 3 includes the scene in which the company A server 101 transmits the request information for requesting exercise to the company B server 111 ("(e) Requesting exercise (walk)"), and in response to this, the company B server 111 transmits to the robot 110 the instruction information requesting exercise ("(f) Inducing and instructing to exercise (walk)"). The request information transmitted in this scene includes urgency degree information. The urgency degree information is information indicating degree of urgency (urgency degree) for the user to exercise. The company B server 111 that receives the request information manages necessary urgency degree information. The necessary urgency degree information is information indicating urgency degree (necessary urgency degree) that becomes necessary for the robot 110 to execute the requested task.

The necessary urgency degree is used to cancel a request with a low urgency degree for the user, the request being made by other company (for example, the company A) via the robot 110, such as while the user is concentrating on some specific work, or to suspend execution of the request till a timing when the encouragement is appropriate. The necessary urgency degree information is information held by the company B server 111 or the robot 110 and used by the company B server 111 or the robot 110. The urgency degree indicated by the urgency degree information included in the request information that is requested to the robot 110 by another company (for example, the company A) is also set in accordance with the same criteria as those for the necessary urgency degree information. As illustrated in FIG. 6, the necessary urgency degree may be set in stages such as high, medium, and low.

"High": When the necessary urgency degree is "high", a request that notifies the user of information with high urgency concerning life, health, danger, or risk of property loss is processed. Otherwise, the request is suspended or rejected.

"Medium": When the necessary urgency degree is "medium", a request that notifies the user of important information in the daily life is processed, in addition to the request whose necessary urgency degree is classified as "high". Otherwise, the request is suspended or rejected. The important information in the daily life includes, for example, information for notifying the user of a next schedule, and information for notifying the user of a state at risk of significant loss (for example, leaving a gas oven on).

"Low": When the necessary urgency degree is "low", all requests are executed.

As such, when the necessary urgency degree is set high, among requests received by the company B server 111 from the server of another company (the company A server 101), only a request that is critical and urgent to the user is processed immediately. Any other requests are suspended or rejected. The urgency degree information included in the request information that is critical and urgent to the user is given by the other company (company A), which is the source, in accordance with the definition of the necessary urgency degree as described above.

More specifically, if the urgency degree information (high, medium, or low) included in the request information transmitted by the server of the other company (for example, the company A server 101) is equal to or higher than the necessary urgency degree information (high, medium, or low) set for the company B (for example, the company B server 111), a request indicated by that request information is processed immediately. Otherwise, the request is not executed immediately and suspended till the appropriate timing or rejected.

As noted above, in order to realize the scenario of providing the capabilities of the robot 110 in the health management as illustrated in FIG. 3, a description has been given of the cooperation setting between the company A and the company B, the access rights to the robot capabilities of the company A, and the urgency degree of the requests. Hereinafter, an overall flow of processing for realizing this scenario by using them is described.

Figure 7:
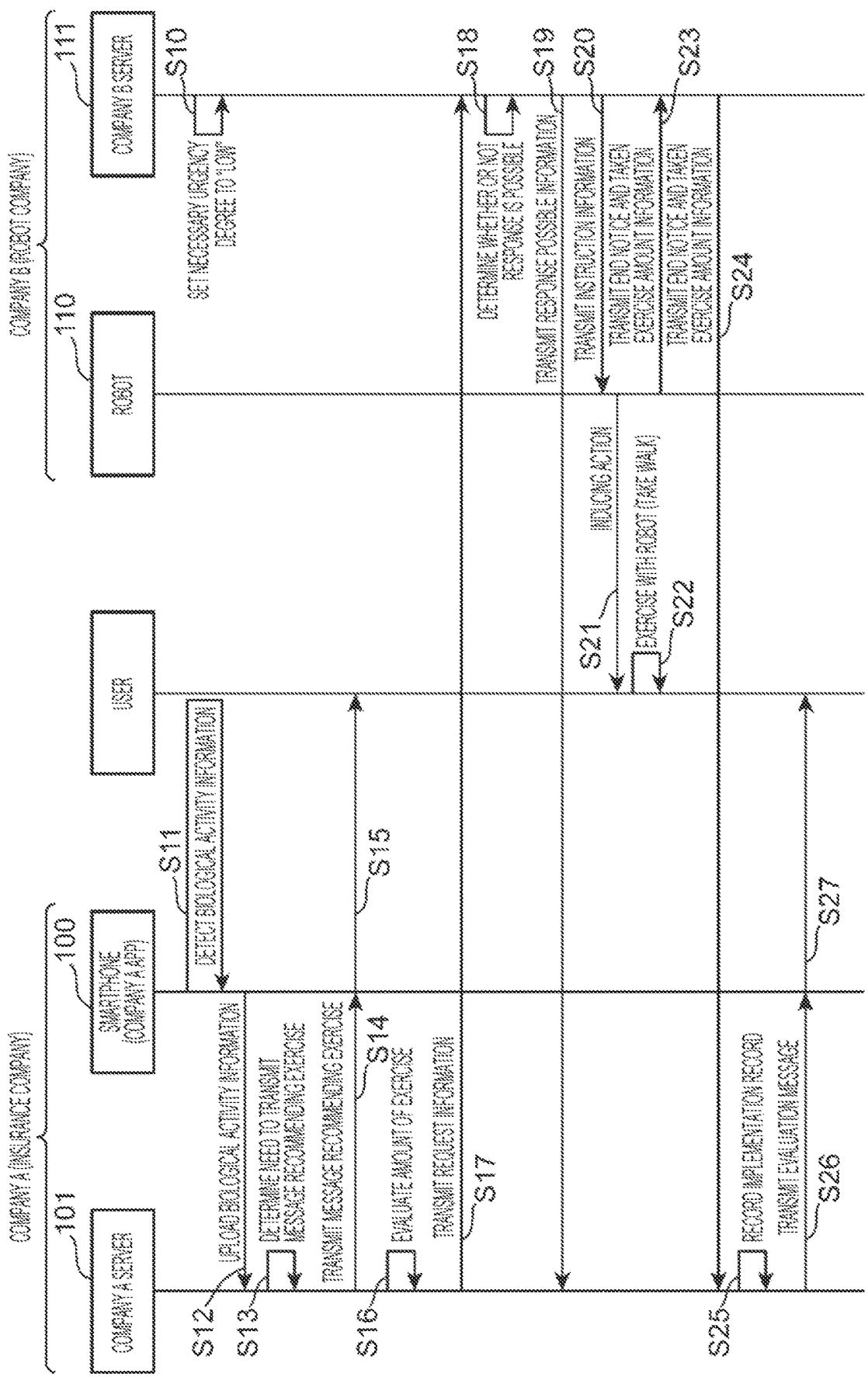
FIG. 7 is a flowchart illustrating an example of processing in which the non-robot company requests a task from the robot.

FIG. 7 is a flowchart illustrating an example of a process in which the non-robot company requests a task from the robot 110. In particular, FIG. 7 illustrates a case where the request is immediately executed.

As also illustrated in FIG. 3, the application of the insurance company A (the company A app) that is installed in the smartphone 100 continuously detects the biological activity information of the user and accumulates the detected biological activity information in the memory in the smartphone 100 (step S11). Furthermore, the company A app periodically uploads the accumulated biological activity information to the company A server 101 (step S12). The company A server 101 that has received the biological activity information determines a need to transmit a message (nudge) recommending the user to exercise, based on an insurance contract between the user and the company A (step S13). If it is determined that there is the need to transmit the nudge, the company A server 101 transmits the nudge (step S14). On the contrary, if it is determined that there is no need to transmit the message recommending exercise, the company A server 101 continues a process of accumulating the biological activity information of the user that is uploaded from the company A app.

In step S15, the smartphone 100 displays the message recommending exercise. This presents the message recommending exercise to the user.

In step S16, even after displaying the message recommending exercise, the company A app and/or the company A server 101 continuously detects the biological activity information of the user, calculates the amount of exercise taken by the user based on the detected biological activity information, and evaluates the calculated amount of exercise.

The company A server 101 determines a need to encourage the user to exercise more strongly, based on the insurance contract between the user and the company A. Here, if a state is observed more than or equal to a predetermined number of times in which the amount of exercise taken by the user calculated in step S16 is less than the target amount of exercise, the company A app and/or the company A server 101 determines that stronger encouragement is needed since the nudge did not improve the amount of exercise taken by the user. Here, it is assumed that the determination is made that the stronger encouragement is needed. On the contrary, if it is determined that the stronger encouragement is not needed, the company A server 101 continues the process of accumulating the biological activity information of the user that is uploaded from the company A app. Here, for example, if the state is not observed more than or equal to a predetermined number of times in which the amount of exercise taken by the user calculated in step S16 is less than the target amount of exercise, the company A app and/or the company A server 101 determines that stronger engagement is not needed The company A server 101 that determined in step S17 that the stronger encouragement is needed transmits to the company B server 111 the request information requesting the robot 110 for the task of encouraging the user to exercise.

The request information includes the unique ID of the company A app of the user, the urgency degree information indicating urgency degree of the request, suspension period information indicating a suspension period till the request is executed, and content of the request. The content of the request indicates, for example, a task that is requested to the robot 110. The company B server 111 that has received the request information can identify the unique ID of the company B app corresponding to the unique ID of the company A app, from the unique ID of the company A app included in the request information. Since the company B server 111 manages the robot ID of the robot 110 corresponding to the unique ID of the company B app, it is possible to uniquely identify the robot 110 that is to execute the task requested by the company A.

Furthermore, the request information includes the target amount of exercise needed by the user. The target amount of exercise is, for example, 5000 steps per day or 150 Kcal of calories burned in a day, or the like. In this example, the target amount of exercise is 5000 steps per day, and the current amount of exercise by user is 2000 steps per day. To urge the user to take a walk of 5000 steps per day, the company A server 101 transmits the request information to the company B server 111. In addition, the urgency degree indicated by the urgency degree information included in this request information is "low".

In step S18, the company B server 111 that has received the request information determines whether or not response to the request is possible. The company B server 111 has set the necessary urgency degree indicated by the necessary urgency degree information to "low" before receiving this request information (step S10). Thus, the company B server 111 compares the urgency degree indicated by the urgency degree information included in the received request information with the necessary urgency degree indicated by the preset necessary urgency degree information to determine whether or not response to the request is possible. Here, since the urgency degree indicated by the urgency degree information included in the request information is "low", the necessary urgency degree indicated by the necessary urgency degree information is "low", and the urgency degree indicated by the urgency degree information is equal to or higher than the necessary urgency degree indicated by the necessary urgency degree information, the company B server 111 determines that the request indicated by this request information be immediately executed. Therefore, the company B server 111 transmits to the company A server 101 response possible information indicating that the request will be responded (step S19). The request information and the necessary urgency degree information are examples of the first information.

The company B server 111 that has transmitted the response possible information transmits to the robot 110 the instruction information instructing the robot 110 to take an inducing action to urge the user to exercise that is equal to or larger than the target amount of exercise (step S20). This inducing action is the action of the robot 110 such as telling the user "Let's go for a walk" or bringing the lead and asking for going for a walk, as described above. Depending on the appearance and motor abilities of the robot 110, various forms of the inducing actions are used.

The instruction information may include validity period information indicating the period of validity. The period of validity is, for example, 10 minutes. If the robot 110 continues to ask the user to go for a walk for the period of validity based on the instruction information but the user does not respond, the robot 110 may automatically stop the inducing action. Furthermore, if the behavior change of the user does not succeed in this manner, the robot 110 may take the inducing action again after a certain period of time has elapsed, or while the user is relaxing. In addition, the period of validity of the inducing action in this case may be shorter than the period of validity of the last inducing action that failed. The reason for setting the period of validity shorter is that a relationship between the user and the robot may deteriorate if the failed inducing action is repeated in the same manner.

The robot 110 that has received the instruction information from the company B server 111 takes the inducing action to take the user out for exercise (taking a walk of 5000 steps per day) according to the instruction information (step S21). In this example, since the robot 110 is the dog-shaped robot, it takes the inducing action of wagging its tail while barking "bow-wow". This inducing action can remind the user of walk. Besides, the robot 110 may repeat the inducing action of talking to the user in a language understandable by the user, such as " Let's take a walk" or "I want to go for a walk" or the like, and/or the inducing action of showing the intention of going for a walk by bringing the lead used for the walk, during the period of validity.

If the company A server 101 has the access right to the sensor 110c or the motor abilities of the robot 110 and seeks direct access to the motor abilities, the company A server 101 analyzes a surrounding situation of the robot 110, and, based on a result of the analysis, may transmit a command to control the facial expressions, the vocalization, the posture, and the movement of the robot 110 to the robot 110 directly or via the company B server 111. Consequently, the company A server 101 can directly control the robot 110.

In response to these inducing actions from the robot 110, the user makes a decision to take a walk and takes exercise (a walk) with the robot (step S22). According to the instruction information from the company B server 111 that instructs the walk of 5000 steps, the robot 110 proposes a walking course to the user, and/or may lead the walking by itself, so that the number of steps of the walk will be 5000 steps.

In a case where the robot 110 does not have the ability to walk with the user, such as being small or having no function to walk, the robot 110 may propose the walking course to the user, so that the number of steps of the walk will be 5000 steps. In this case, the robot 110 may take the inducing action to encourage the user so that the use achieves the target amount of exercise. For example, the robot 110 may speak such as "Let's stop by the nearby supermarket newly opened" or "If you climb the hill tonight, you may be able to see a shooting star". This adjusts the number of steps of the walk (amount of exercise).

In this manner, if the robot 110 senses by the camera image or the position sensor or the like that the user has returned home after successfully taking exercise (a walk), the robot 110 transmits to the company B server 111 an end notice indicating that the exercise (walk) with the user has ended and the taken exercise amount information indicating the amount of exercise taken in the exercise (step S23). The taken exercise amount information includes information indicating, for example, the number of steps, the walking course, and a pace of the walk.

The company B server 111 transmits the end notice of the request and the taken exercise amount information to the company A server 101 (step S24). The company A server 101 that has received the end notice and the taken exercise amount information records, in the memory 101c, information indicating the requested exercise was taken and the taken exercise amount information, as an implementation record (step S25).

If the company A server 101 determines that the amount of taken exercise indicated by the taken exercise amount information is equal to or larger than the target amount of exercise indicated by target exercise amount information, the company A server 101 transmits to the smartphone 100 the evaluation message indicating that the user has achieved the target amount of exercise (step S26). The smartphone 100 that has received the evaluation message displays the evaluation message indicating that the target amount of exercise has been achieved, through the company A app (step S27). As a result, the user can obtain a certain sense of achievement and reduce the sense of resistance to exercise (walk). Note that if the amount of taken exercise is less than the target amount of exercise, the company A server 101 may transmit an evaluation message indicating accordingly to the smartphone 100.

Here, although the case where the request inducing to exercise is immediately executed is described, there is a case where the user cannot immediately respond to encouragement from the robot 110 during a business meeting or the like.

Figure 8:
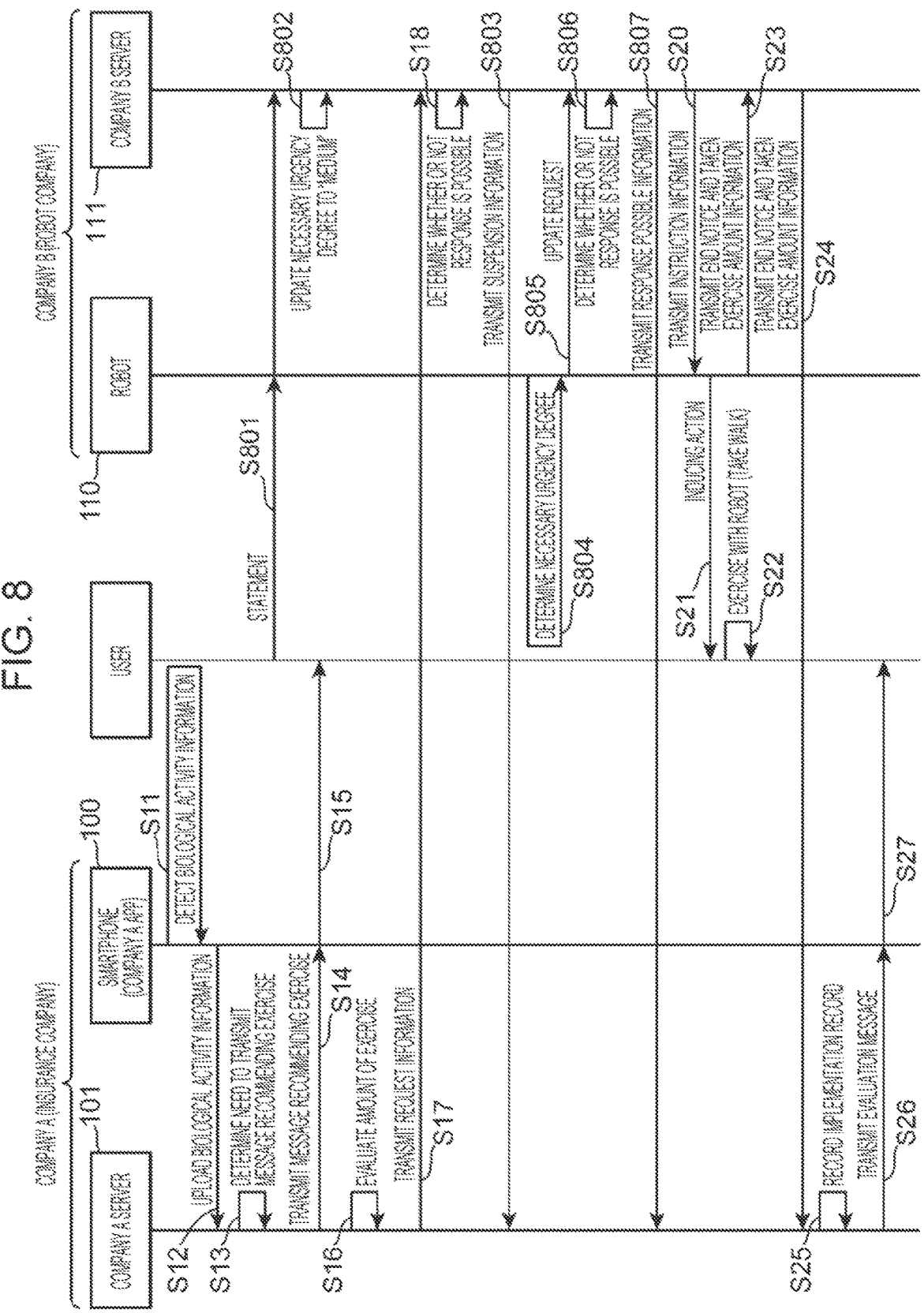
FIG. 8 is a flowchart illustrating an example of processing in which the non-robot company requests a task from the robot.

FIG. 8 is a flowchart illustrating an example of a process in which the non-robot company requests a task from the robot 110. In particular, FIG. 8 illustrates a case where a request is not executed immediately. FIG. 8 differs from FIG. 7 in the necessary urgency degree information when the company B server 111 receives the request information. In FIG. 7, the necessary urgency degree indicated by the necessary urgency degree information is "low" where any request is immediately executed by the robot 110. On the other hand, in FIG. 8, the necessary urgency degree indicated by the necessary urgency degree information is "medium". Unless the urgency degree indicated by the urgency degree information included in the request information is "medium" or "high", the request is not immediately executed. In this case, the request is suspended till an appropriate timing or rejected. FIG. 8 exemplarily illustrates a case where the request is suspended till the appropriate timing.

The process in which the company A continuously detects the biological activity information of the user using the company A app and the company A server 101 and transmits to the company B server 111 the request information with "low" urgency degree requesting the user to exercise (equivalent to 5000 steps in a walk) is same as that of FIG. 7 and thus a description thereof is omitted. A difference lies before the process (step S17) in which this request information is transmitted.

In step S801, the robot 110 determines on a statement of the user who has an intention of not communicating with the robot 110 or the user's situation. In step S802, the robot 110 updates the necessary urgency degree to "medium" (one example of a predetermined level) based on a result of the determination on the statement or the situation.

For example, when the user makes a statement to the robot 110 with the intention of not communicating with the robot 110, such as "Keep quiet" or "Don't talk to me", the robot 110 only has to change the necessary urgency degree from "low" to "medium". Alternatively, when the robot 110 has recognized from sensing data of the sensor 110c that the user is talking or driving a car, the robot 110 may change the necessary urgency degree from "low" to "medium". The robot 110 that has changed the necessary urgency degree to "medium" transmits an update request for updating the necessary urgency degree to "medium" to the company B server 111. The company B server 111 that has received this update request updates the necessary urgency degree from "low" to "medium" (step S802).

The company B server 111 that has received the request information from the company A server 101 determines whether or not response is possible, based on the urgency degree and the necessary urgency degree included in the request information (step S18). Here, since the "low" urgency degree is lower than the "medium" necessary urgency degree, the company B server 111 determines that the request cannot be executed immediately. The company B server 111 that has determined that the request cannot be executed immediately transmits to the company A server 101 suspension information indicating that the request has been suspended (step S803).

Subsequently, the robot 110 continuously performs a process to determine whether or not it is necessary to change the necessary urgency degree, based on the user's statement and the sensing data from the sensor 110c (step S804). When the user expressly makes a statement that lowers the necessary urgency degree, when the user makes a statement including a topic which is not urgent, or when it is determined that the user takes on behavior with low urgency, the robot 110 may set the necessary urgency degree to "low". The behavior with low urgency is, for example, behavior such as watching TV, operating a smartphone, or the like.

When the necessary urgency degree is updated from "medium" to "low", the robot 110 transmits to the company B server 111 the update request for updating the necessary urgency degree to "low" (step S805).

The company B server 111 that has received the update request changes the necessary urgency degree from "medium" to "low". Next, the company B server 111 determines again whether or not response to the request that is being suspended is possible (step S806). Here, since the urgency degree indicated by the urgency degree information included in the request information transmitted from the company A server 101 in step S803 is "low", the necessary urgency degree indicated by the current necessary urgency degree information is "low", and the urgency degree is equal to or higher than the necessary urgency degree, the company B server 111 transmits the response possible information to the company A server 101 (step S807).

Since subsequent processing is the same as that of FIG. 7, a description thereof is omitted.

As described with reference to FIG. 7 and FIG. 8, the mechanism of the company B server 111 is summarized as follows. The company B server 111 causes the robot 110 of the company B, which is familiar to the user, to execute a request that needs the motor abilities of the sensor 110c or the robot 110 that are not held by the company A (company A app). The company B server 111 performs the cooperation setting between the company A and the company B for each user. Based on the user's advance input, the company B server 111 registers in advance the access right setting information that defines to what extent the respective capabilities of the robot 110 of the company B are to be used by the company A. When the user is in the situation in which the user cannot care about the robot 110, the company B server 111 suspends or rejects a request with a low urgency degree. The company B server 111 re-executes the suspended request at an appropriate timing, in response to a request from the user or any change in the user's situation.

Figure 9:
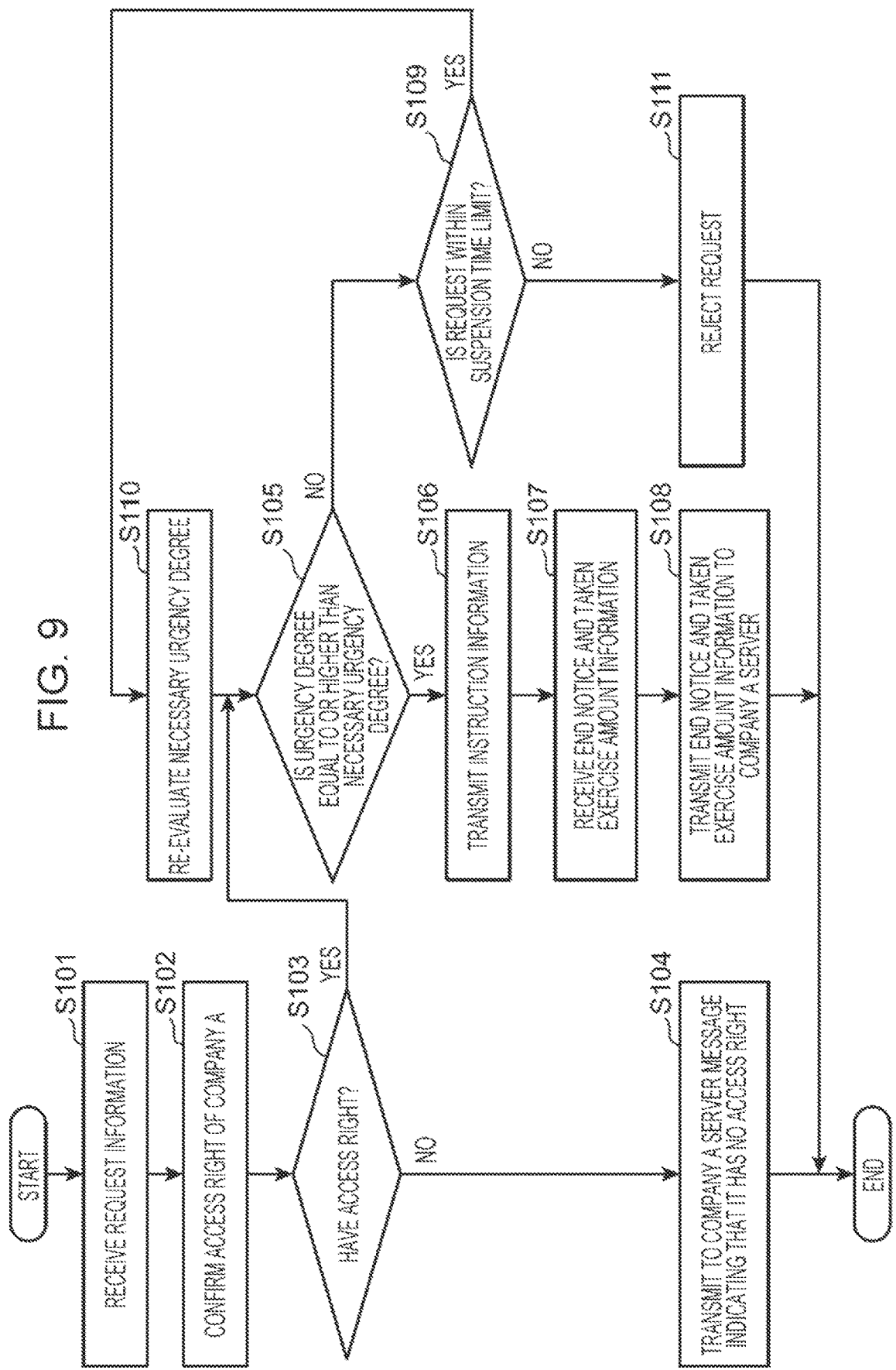
FIG. 9 is a flowchart illustrating an example of processing of a company B server.

FIG. 9 is a flowchart illustrating an example of processing of the company B server 111. In the processing of FIG. 9, the company B server 111 determines whether or not the non-robot company (company A) has the access right necessary for carrying out a requested task, whether or not there is urgency to immediately execute the task requested for the user, and whether or not the request execution of which is suspended exceeds the suspension period, and responds to the request of the non-robot company (company A) based on the determination result. Specifically, the processing is as follows.

In step S101, the company B server 111 receives from the company A server 101 the request information requesting the robot 110 for the task of encouraging the user to exercise.

In step S102, the company B server 111 confirms the access right of the company A to the requested task. First, the company B server 111 determines whether or not the pair information in which the unique ID of the company A app that is included in the request information is associated with the unique ID of the company B app has been pre-registered in the memory 111c. Then, when the company B server 111 determines that the pair information has been pre-registered, the company B server 111 confirms based on the access right setting information illustrated in FIG. 5 whether or not the company A holds the access right to the task requested by the request information. Here, since the permission level of the access right of the company A for the task of "Inducing to exercise" illustrated in FIG. 5 is set to "1" or "2", it is determined that the company A has the access right to the requested task. Note that if the permission level of the access right of the company A to the task of "Inducing to exercise" is "0", it is determined that the company A has no access right.

If it is determined that the company A has no access right (NO in step S103), the company B server 111 transmits to the company A server 101 a message indicating that the company A has no access right to execute the requested task (step S104), and the processing ends.

On the other hand, if it is determined that the company A has the access right (YES in step S103), the company B server 111 compares the urgency degree indicated by the urgency degree information included in the request information that is received in step S101 with the corresponding necessary urgency degree of the user currently set, and determines whether or not to execute the request indicated by the request information immediately (step S105).

If the urgency degree is less than the necessary urgency degree (NO in step S105), the company B server 111 determines whether or not time elapsed since receipt of the requested information is within the suspension period (step S109).

The suspension period is time information indicating how long the request execution of which is suspended is to be suspended. When the elapsed time from receipt of the request information exceeds the suspension period (NO in step S109), the company B server 111 rejects the request indicated by that request information (step S111). The company B server 111 that has rejected the request transmits to the company A server 101 that made the request, a message that the request has been rejected as the suspension period was exceeded, and the processing ends.

This prevents a large number of accumulated requests with the "low" urgency degree from being executed all at once at the moment when the necessary urgency degree is updated to "low". Furthermore, it prevents execution of requests which is currently meaningless because a long time has passed since the requests were received. Rejection of such requests is needed to maintain the effect of encouragement to the user by the robot 110.

On the other hand, when the elapsed time from receipt of the request information is within the suspension period (YES in step S109), the company B server 111 acquires state data of the user via the robot 110 and re-evaluates the current necessary urgency degree via the robot 110, based on the acquired state data (step S110). Alternatively, the robot 110 may acquire the state data of the user, set the current necessary urgency degree by itself based on the acquired state data, and notify the company B server 111. When the processing of step S110 ends, the processing returns to step S105. As a result, the loop processing illustrated in steps S105, S109, and S110 is performed. With this loop processing, only requests with the urgency degree that is equal to or higher than the necessary urgency degree that becomes necessary for encouraging the user are executed as needed, and execution of requests that do not have the urgency degree that is equal to or higher than the necessary urgency degree that becomes necessary for encouraging the user continues to be suspended during the suspension period. The state data is data that dynamically varies in relation to the user's state sensed by the robot 110. Specifically, as illustrated in FIG. 9 below, the state data includes the necessary urgency degree information that is set based on the sensing data by the sensor 110c of the robot 110.

When the urgency degree indicated by the urgency degree information included in the request from the company A server 101 is equal to or higher than the necessary urgency degree managed by the company B server 111 or the robot 110 (YES in step S105), the processing proceeds to step S106.

In step S106, when the user is in a state in which the user may be encouraged to exercise, the company B server 111 transmits the instruction information instructing the robot 110 to execute the task requested from the company A server 101. The robot 110 that has received the instruction information executes the task according to the instruction information. As a result, the robot 110 takes the inducing action to take the user out for a walk. The user who has decided to take a walk by this inducing action takes a walk with the robot 110. The robot 110 that has returned from the walk transmits to the company B server 111 a task execution result, the end notice informing the end of the walk, and the taken exercise amount information in the walk. As a result, the company B server 111 receives the end notice and the taken exercise amount information (step S107).

In step S108, the company B server 111 transmits the received end notice and taken exercise amount information to the company A server 101.

Note that if the company A server 101 has the access rights to the sensor 110c, the ability to change facial expressions, the ability to vocalize, the ability to change posture, and/or the ability to move, which are the motor abilities, for the robot 110, the company A server may directly control the facial expressions, the voice utterance, the posture, and/or the movement of the robot 110, according to the surrounding conditions of the robot 110 via the company B server 111. Also in this case, the robot 110 instructed by the company B server 111 to execute the task may transmit the task execution result to the company B server 111. That is, although the company A server 101 remotely controls the robot 110, it is the company B server 111 that directly controls the robot 110, and the relationship between the robot 110 and the company B server 111 is the same as the aspect described above.

It is expected that remote control of the robot 110 by the company A server 101 will be realized in the future by establishing high-speed and low-latency wireless communication infrastructure called "5G" or "Beyond 5G", or the like. The company B server 111 that has received the task execution result transmits the execution result to the company A server 101, which is the request source of the task, and the processing ends.

FIG. 10 is a table illustrating an example of setting of the necessary urgency degree. FIG. 10 illustrates a transition in the user's states from 8'oclock in the morning to 8'oclock in the evening. Although in the following description, a description is given assuming that the robot 110 sets the necessary urgency degree, this is an example, and the company B server 111 may set. In this case, the company B server 111 may set the necessary urgency degree based on the sensing data acquired via the robot 110.

The robot 110 continuously senses the user's state, detects the user's state from the sensing result, as needed, and updates the necessary urgency degree appropriately based on the detection result.

During a time zone from 8:00 to 10:00, the user is talking with another person face-to-face. Using the sensor 110c such as the camera and the microphone or the like, the robot 110 determines that the user is talking with the other person. A neural network has been developed that determines or explains human behavior and states from still images, moving images, or audio. Therefore, using an image recognition technique or an audio recognition technique based on such a neural network, the robot 110 may detect the user's state. After determining that the user's state is talking, the robot 110 sets the necessary urgency degree to "medium". As a result, unless a request has the "medium" or higher urgency degree, the request will no longer be executed. Then, the robot 110 shares the set necessary urgency degree with the company B server 111.

Further in this determination, the robot 110 may also perform a sentiment analysis of the user from conversation content and voice tone, or the like, included in the facial expressions and gestures acquired from the camera and/or audio information acquired from the microphone. Here, results of the sentiment analysis are classified to, for example, "positive", "neutral", and "negative". In the case of conversations for which the result of the sentiment analysis is "positive" or "neutral", it is highly likely that the user will tolerate interruptions by the robot 110 to the conversation to execute the task. In this case, the robot 110 may lower the necessary urgency degree set above. In addition, in the case of the conversation for which the result of the sentiment analysis is "negative", it is highly likely that the user will not tolerate the interruptions to the conversation. Thus, the robot 110 may maintain or increase the necessary urgency degree set above. When the necessary urgency degree is changed, the robot 110 shares the changed necessary urgency degree with the company B server 111.

Adding the sentiment analysis of the user to the determination on the user's state in this manner enables the robot 110 to process the task in a more appropriate timing for the user.

Here, although the results of the sentiment analysis are classified to three categories, the present disclosure is not limited thereto. The results of the sentiment analysis may be classified to more categories such as "delight, anger, sorrow, and pleasure" or fewer categories such as two categories of "positive" and "negative". In addition, the robot 110 may estimate a degree of user's stress and adjust the necessary urgency degree according to a numerical range of the estimated degree of stress.

During the time zone from 10:00 to 12:00, the user is working (working) at a computer. Using the sensor 110c such as the camera, the microphone, or the like, the robot 110 detects that the user is operating the computer. After determining that the user is working at the computer, the robot 110 maintains the necessary urgency degree at "medium". In this case, unless a request has the "medium" or higher urgency degree, the request will not be executed. Then, the robot 110 shares the set necessary urgency degree with the company B server 111.

During the time zone from 12:00 to 13:00, the user is sitting on a chair and having a meal. Using the sensor 110c such as the camera, the microphone, or the like, the robot 110 detects that the user is having a meal. After determining that the user is having a meal, the robot 110 sets the necessary urgency degree to "low" which is the lowest. Then, the robot 110 shares the set necessary urgency degree with the company B server 111.

During the time zone of 13:00 to 15:00, the user is on the phone or in a meeting. Using the sensor 110c such as the camera, the microphone, or the like, the robot 110 detects that the user is talking over a mobile phone (on the phone) or talking over the computer (in the meeting). After determining that the user is on the phone or in the meeting, the robot 110 sets the necessary urgency degree to "medium". In this case, unless a request has the "medium" or higher urgency degree, the request will not be executed. Then, the robot 110 shares the set necessary urgency degree with the company B server 111.

During the time zone from 15:00 to 16:00, the user is exercising. Using the sensor 110c such as the camera, the microphone, or the like, the robot 110 detects that the user is exercising. After determining that the user is exercising, the robot 110 maintains the necessary urgency degree at "medium".

Further in this determination, the robot may measure a periodic change in the user's skin color based on the image acquired from the camera or may measure the user's heart rate by using a smart watch, or the like. When the heart rate measured here is lower than a predetermined value, it is highly likely that the user will tolerate the interruptions by the robot 110 to the exercise to execute the task. In this case, the robot 110 may lower the necessary urgency degree. On the other hand, when the heart rate is higher than the predetermined value, it is highly likely that the user will not tolerate the interruptions by the robot 110 to exercise to execute the task. Therefore, the robot 110 may maintain the necessary urgency degree or increase the necessary urgency degree. When the necessary urgency degree is changed, the robot 110 shares the changed necessary urgency degree with the company B server 111.

When it is determined that the user's state is exercising in this manner, adding the user's heart rate enables the robot 110 to process the task in a more appropriate timing for the user.

During the time zone of 16:00 to 20:00, the user is lying down and relaxing. Using the sensor 110c such as the camera, the microphone, or the like, the robot 110 detects that the user is in a relaxing state. After determining that the user is in the relaxing state, the robot 110 sets the necessary urgency degree to "low" which is the lowest. Then, the robot 110 shares the necessary urgency degree with the company B server 111.

In this manner, the user's state is changing from moment to moment. Utilizing the sensor 110c, the robot 110 senses the user's state and determines the user's state, as needed. Furthermore, the robot 110 updates the necessary urgency degree based on the determination result. When updating the necessary urgency degree, the robot 110 notifies the company B server 111 of the updated necessary urgency degree and shares the most recent necessary urgency degree with the company B server 111. In this manner, the necessary urgency degree varies depending on the user's state, as needed.

As such, according to the present embodiment, when determining that it is necessary to encourage the user to exercise, the company A server 101 can encourage the user to exercise through the robot 110 managed by the company B server 111. Consequently, even though the company A server 101 itself does not control the robot 110, the company A server 101 can cause the robot 110 to take the action to encourage the user to exercise. Therefore, it is possible to give the user the stronger motivation to exercise than a case where the video audio output unit 100f of the user's smartphone 100 merely displays a message urging the user to exercise.

Note that the present embodiment can be employed in the following modification examples.

(1) In step S801 of FIG. 8, the robot 110 may ask the user a question, such as "May I talk to you now?" or "May I bother you a bit?" to confirm he user's current necessary urgency degree, and cause the user to answer. The robot 110 directly asks the user of the questions as described above if the number of requests that have not been executed at a predetermined timing or yet, and/or when the urgency degree thereof meets predetermined conditions, or the like. With these questions, the robot 110 may acquire information for setting the necessary urgency degree, from content of the user's answer. In the case of this method, since the robot 110 can directly confirm with the user about the necessary urgency degree, the robot 110 can set and update the necessary urgency degree information as recognized by the user.

Here, when the user gives a positive answer such as "OK" to the above question, the robot 110 may set the necessary urgency degree to the low level such as "low". In addition, when the user answers such as "Please come later" or when no answer can be obtained, the robot 110 may set the necessary urgency degree to the high level such as "medium" or "high", assuming that it is not the right time to encourage the user.

(2) The smartphone 100 is an example of an information terminal, and in the present disclosure, the information terminal is not limited to the smartphone 100. The information terminal may be a tablet computer and a portable information terminal may be employed.

Robot Configuration and Control Method

In the following, in particular, a description is given of a configuration and a control method of the robot in relation to the embodiments described above.

Note that in the description below, any content that overlaps the description given so far will be omitted as appropriate. However, the configuration and the control method of the robot described below are not limited only to forms based on the contents that have been described so far.

Figure 11:
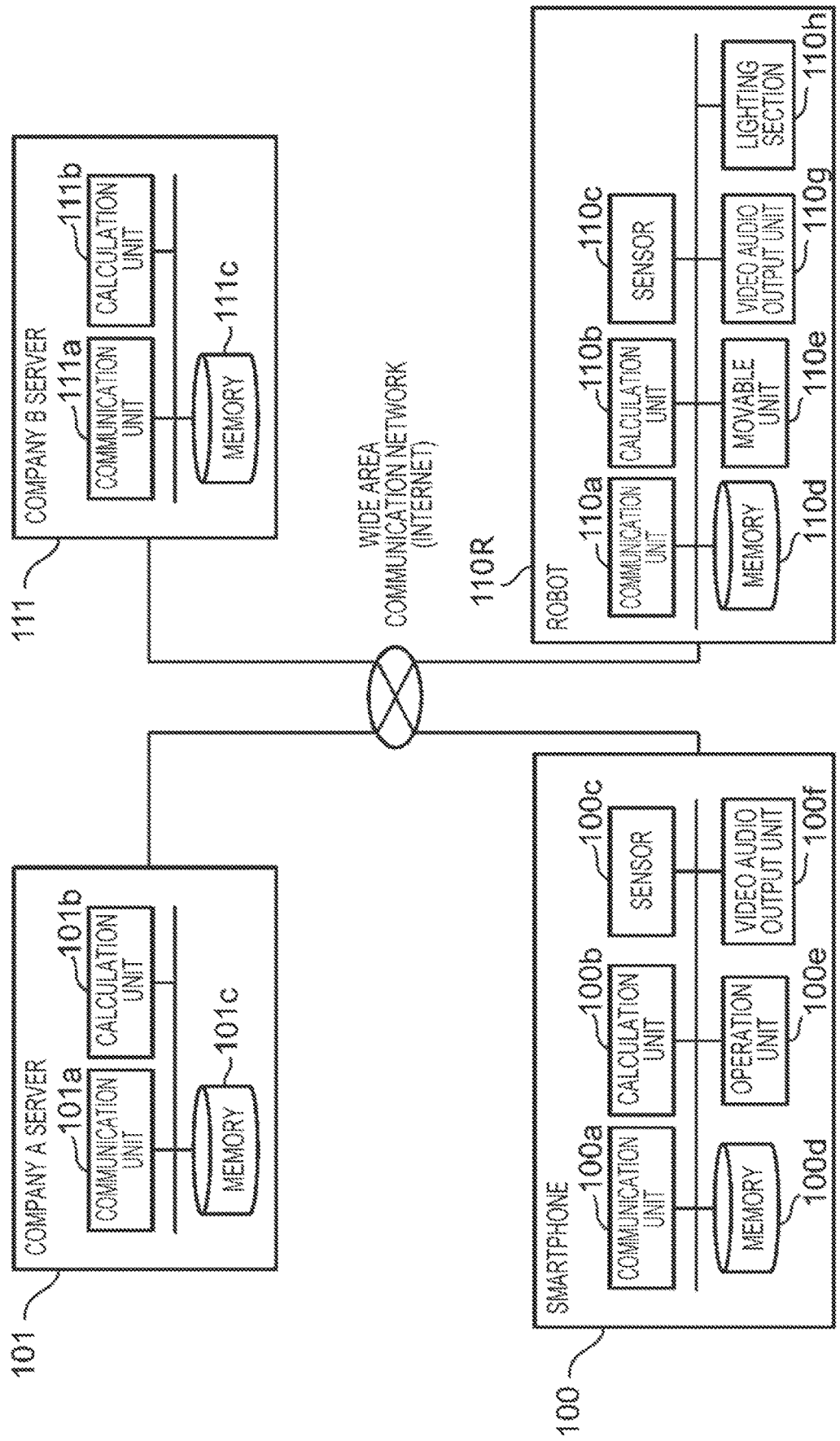
FIG. 11 is a block diagram illustrating an example of an information system configuration according to an embodiment of the present disclosure.

FIG. 11 is a block diagram illustrating an example of a configuration of an information system according to the embodiment of the present disclosure. FIG. 11 differs from the block diagram illustrated in FIG. 2 only in a configuration of a robot 110R. A description of the configuration of the robot 110R is given hereinafter.

The robot 110R includes a communication unit 110a, a calculation unit 110b, a sensor 110c, a memory 110d, a movable unit 110e, a video audio output unit 110g, and a lighting section 110h. The robot 110R differs from the robot 110 depicted in FIG. 2 in that the robot 110R includes the video audio output unit 110g in place of the audio output unit 110f and that the robot 110R further includes the lighting section 110h.

The video audio output unit 110g is a device that outputs a video and/or sound and includes a display and a speaker, for example.

The lighting section 110h includes a light source such as a light-emitting diode (LED) or a laser diode (LD). The lighting section 110h may further include an optical element such as a lens or a mirror to control an irradiation direction of light emitted from the light source. The lighting section 110h may further include an actuator to change the irradiation direction.

The robot 110R can perform various contents of control that have already been described for the robot 110. Stated another way, the description regarding the robot 110 in the present disclosure can be appropriately read as the description regarding the robot 110R.

Figure 12:
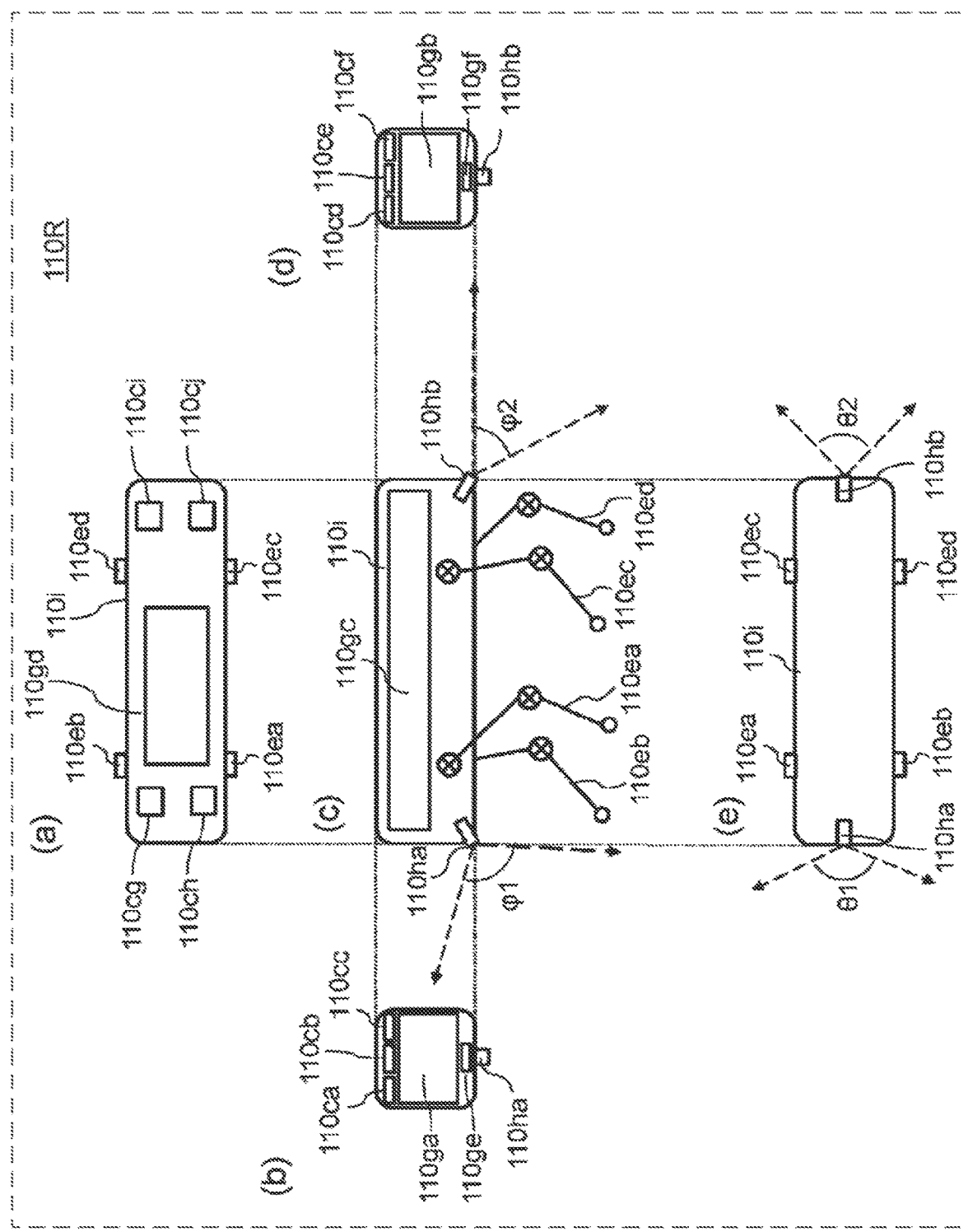
FIG. 12 is a diagram illustrating an example of a robot configuration according to the embodiment of the present disclosure.

FIG. 12 is a schematic diagram that exemplarily illustrating appearance of the robot 110R according to the embodiment of the present disclosure. FIG. 12 includes (a) a top view, (b) a front view, (c) a side view, (d) a back view, and (e) a bottom view. The robot 110R depicted in FIG. 12 is a robot having four legs that moves autonomously.

The robot 110R includes a main body 110i, a pair of front legs 110ea and 110eb, and a pair of rear legs 110ec and 110ed. The front legs 110ea and 110eb and the rear legs 110ec and 110ed are each an example of the movable unit 110e illustrated in FIG. 11, and leg joints are driven by actuators. Note that a depiction of some or all of the legs 110ea, 110eb, 110ec, and 110ed is omitted in (a) the top view, (b) the front view, (d) the back view, and (e) the bottom view in FIG. 12.

The robot 110R includes a lighting unit 110ha provided near the front of the main body 110i and a lighting unit 110hb provided near a back face. The lighting unit 110ha can illuminate an area in front of the robot with a sufficient amount of light, for example, in an irradiation range with a horizontal angle θ1 and an elevation/depression angle φ1. The lighting unit 110hb can illuminate an area behind the robot with the sufficient amount of light, for example, in an irradiation range with a horizontal angle θ2 and an elevation/depression angle φ2. The lighting units 110ha and 110hb are each an example of the lighting section 110h depicted in FIG. 11.

The robot 110R includes a display 110ga provided on the front of the main body 110i, a display 110gb provided on the back face, a display 110gc provided on a side face, and a display 110gd provided on a top face. The displays 110ga, 110gb, 110gc, and 110gd are provided for the robot 110R to communicate with the user or a person around the robot 110R through displays of text messages or video information, and display a state of the user or a state of the robot. The robot 110R includes a speaker 110ge provided on the front of the main body 110i and a speaker 110gf provided on the back face. The speakers 110ge and 110gf are provided for the robot 110R to communicate with the user or the person around the robot 110R via output of audio messages or music, and notify the state of the user or the state of the robot.

The displays 110ga, 110gb, 110gc, and 110gd and the speakers 110ge and 110gf are each an example of the video audio output unit 110g depicted in FIG. 11.

The robot 110R includes an RGB camera 110ca, a ranging sensor 110cb, and an infrared camera 110cc on the front of the main body 110i, and includes an RGB camera 110cd, a ranging sensor 110ce, and an infrared camera 110cf on the back face of the main body 110i. The RGB cameras 110ca and 110cd enable space recognition or object identification. The ranging sensors 110cb and 110ce enable sensing of a shape of an object such as a hazardous object or a shape of a surrounding environment such as concavity and convexity on a road surface or the like. The infrared cameras 110cc and 110cf enable sensing of a person in an environment of low illuminance. Combining these enables the robot 110R to accurately sense surrounding conditions with precision. The RGB cameras 110ca and 110cd, the ranging sensors 110cb and 110ce, and the infrared cameras 110cc and 110cf are each an example of the sensor 110c depicted in FIG. 11.

The robot 110R includes microphones 110cg and 110ch provided near the front of the main body 110i and microphones 110ci and 110cj provided near the back face. Provision of the microphones 110cg, 110ch, 110ci, and 110cj at four locations makes it possible to identify a position of a sound source. The microphones 110cg, 110ch, 110ci, and 110cj are each an example of the sensor 110c depicted in FIG. 11.

Note that the robot according to the embodiment of the present disclosure is not limited to the robot 110R depicted in FIG. 11 or FIG. 12, and may be any robot as far as the robot has a unit and can move autonomously. For example, the robot may have wheels in place of legs. For example, the robot may include a mechanically movable part other than a leg joint.

Figure 13:
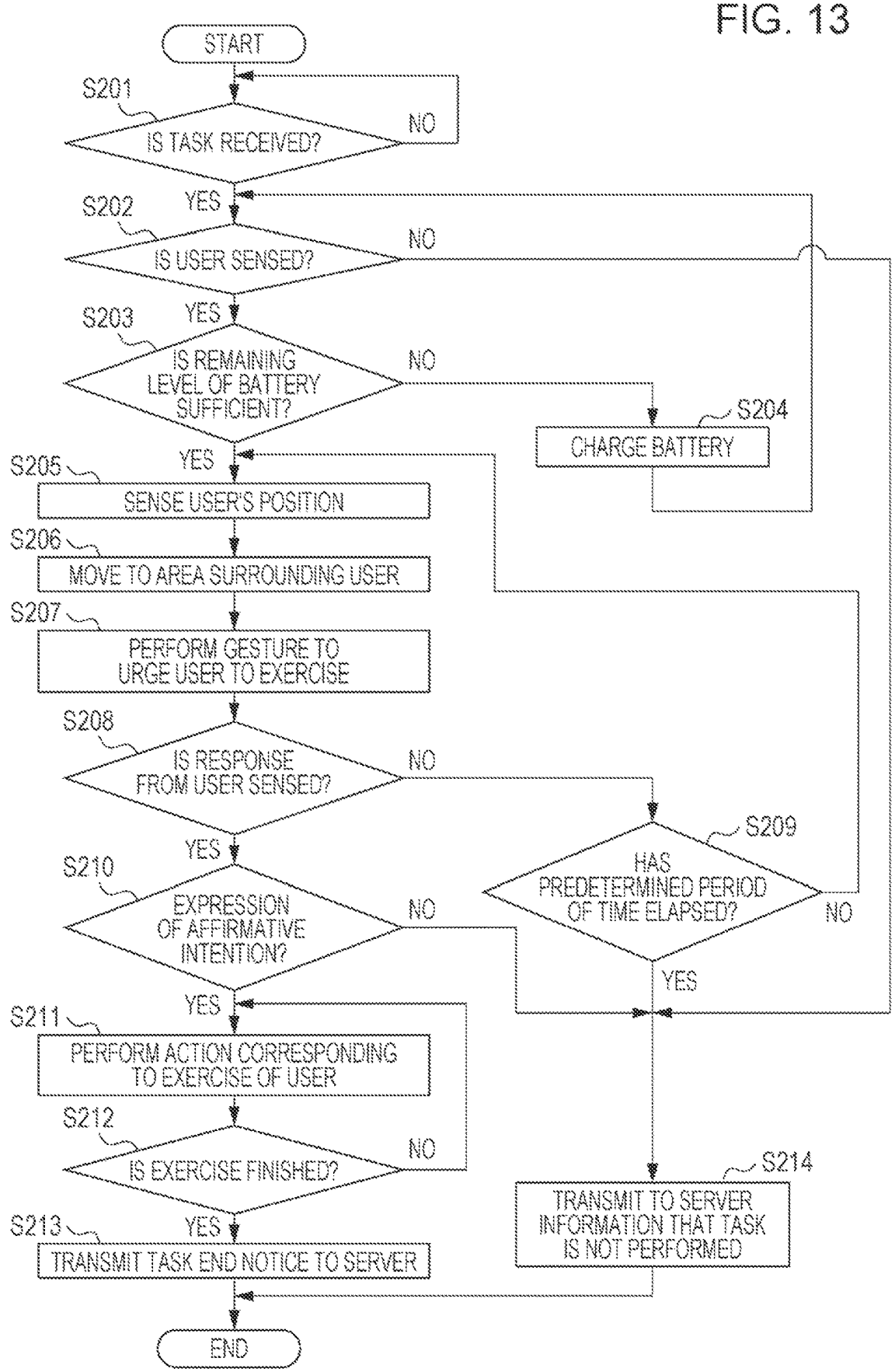
FIG. 13 is a flowchart illustrating an example of processing performed by the robot according to the embodiment of the present disclosure.

FIG. 13 is a flowchart illustrating an example of processing performed by the robot according to the embodiment of the present disclosure. FIG. 13 describes a series of operation steps, by the robot 110R, of receiving a task for inducing a user A to exercise from a server (S201), of inducing the user A to exercise (S202 to S210), of performing a predetermined action accompanying exercise of the user A (S211), and of reporting a result to the server (S213 and S214).

The step of receiving the task (S201) corresponds to, for example, step S20 in FIG. 7 or FIG. 8. The steps of inducing to exercise (S202 to S210) correspond to, for example, step S21 in FIG. 7 or FIG. 8. The step of performing the action involved in the exercise (S211) corresponds to, for example, step S22 in FIG. 7 or FIG. 8. The steps of reporting the result to the server (S213 and S214) correspond to, for example, step S23 in FIG. 7 or FIG. 8. Alternatively, the series of the operation steps (S201 to S214) illustrated in FIG. 13 are performed by the robot 110R, between step S106 and step S107 in the flowchart of the company B server 111 illustrated in FIG. 9, for example.

In the following, a description is given of an action of each step with reference to FIG. 13.

In step S201, it is determined whether or not the robot 110R has received the task from the company B server 111. The reception of the task is performed by, for example, the communication unit 110a of the robot 110R receiving instruction information from the company B server 111 and the calculation unit 110b receiving contents of the task included in the instruction information. Here, as an example, a description is given on the assumption that the task is a task of inducing the user A to take a walk. This task may be, for example, a request received by the company B server 111 from the Company A server 101 and transformed into one unit of task that can be processed by the computer system. If the robot 110R has received the task (YES in step S201), the processing proceeds to the next step S202. On the contrary, if the robot 110R has not received the task, the robot 110R waits until the robot 110R receives the task (NO in step S201).

In step S202, the robot 110R determines whether or not the user A, who is a target of the task, has been sensed in its surroundings. For example, the RGB cameras 110ca and 110cd and/or the infrared cameras 110cc and 110cf take images of the surroundings, and the calculation unit 110b determines by the image recognition whether or not the user A appears in the taken images. If the user A has been sensed (YES in step S202), the processing proceeds to the next step S203. If the user A has not been sensed (NO in step S202), the processing proceeds to step S214. In this case, in step S214, the robot 110R transmits to the company B server 111 information that it is impossible to perform the task because the user A cannot be sensed in the surroundings of the robot 110R.

Next, in step S203, the robot 110R determines whether or not remaining level of a battery (not illustrated) mounted on the robot 110R is an amount sufficient for performing the task. For example, information on an amount of power necessary for the task may be estimated by the calculation unit 110b of the robot 110R based on the contents of the task. Alternatively, that information may be included in advance in the instruction information received in step S201. The calculation unit 110b acquires information on the remaining level of the battery from a battery management IC built into the battery, and determines whether the remaining level of the battery is larger than power consumption necessary for the task. If the remaining level of the battery is sufficient (YES in step S203), the processing proceeds to the next step S205. If the remaining level of the battery is insufficient (NO in step S203), the battery is charged until the remaining level of the battery exceeds the amount of power necessary for the task (step S204), and the processing returns to step S202.

Note that step S203 may be performed between step S201 and step S202, or may be performed between step S205 and step S206 to be described below. Alternatively, step S203 may be omitted.

In step S205, the robot 110R senses a position of the user A, using the sensor 110c. For example, the robot 110R takes images of the user A, using the RGB cameras 110ca and 110cd and/or the infrared cameras 110cc and 110cf, and measures a distance from the robot 110R to the user A, using the ranging sensors 110cb and 110ce. This enables the position of the user A to be sensed in a three-dimensional space. Alternatively, the robot 110R may acquire the position of the user A by communicating with a wearable device (not illustrated) worn by the user A. A determination may be made based on radio wave intensity of a radio signal that is transmitted by the wearable device and received by the communication unit 110a of the robot 110R, or current position information, which is acquired by the wearable device via a satellite positioning system, or the like, may be transmitted or responded to the robot 110R.

Note that step S205 may be performed in conjunction with the sensing of the user A of step S202, for example.

In step S206, the robot 110R moves to an area near the user A (that is, a nearby area). The nearby area is a predetermined area that includes the user's current position. The nearby area may be set to, for example, an area within a predetermined distance from the current position of the user A or may be set to an area in a visual field of the user A estimated from the image in which the user A appears. The robot 110R autonomously moves to the nearby area of the user A, driving the movable unit 110e, for example, the four legs 110ea, 110eb, 110ec, and 110ed.

In step S207 the robot 110R preforms the gesture to urge the user A to exercise. Such a gesture may be a gesture of the robot 110R to communicate to the user A its intention that it wishes to take a walk, for example. Examples of the gesture include an action to carry a tool necessary for a walk, such as a harness or a lead or the like, to the nearby area, an action to touch the body of the user A with the front legs 110ea and 110eb, an action to tilt the main body 110i forward to extend the rear legs 110ec and 110ed, or an action to run around in the nearby area. These actions are realized by controlling the actuators that drive the legs 110ea, 110eb, 110ec, and 110ed and/or another actuator that changes a shape or a posture of the robot 110R. In step S207, the robot 110R may present a message for urging the user A to exercise by using the video audio output unit 110g, in addition to or in place of the gesture.

Note that step S207 may be performed in parallel with the movement action of step S206.

In step S208, the robot 110R determines whether or not a response from the user A has been sensed. For example, using the RGB cameras 110ca and 110cd and/or the infrared cameras 110cc and 110cf, the robot 110R monitors a change in the posture of the user A by the calculation unit 110b, and determines that the response from the user A has been sensed, if at least one of the following is satisfied: (i) when magnitude of the change in the posture of the user A exceeds a predetermined threshold, (ii) when it is determined that the posture of the user A is a pose representing expression of a specific intention (for example, sticking his or her thumb up), (iii) when a probability of estimation of emotion of the user A based on his or her facial expressions exceeds a predetermined threshold, or (iv) when it is determined that a temporal change of the posture of the user A is a gesture (for example, shaking his or her head vertically or horizontally) representing expression of a specific intention. Alternatively, the robot 110R monitors voice spoken by the user A using the microphones 110cg, 110ch, 110ci, and 110cj, and determines that the response from the user A has been sensed when volume of the voice spoken by the user A exceeds a predetermined threshold. Each of the threshold values is set to a level that is considered as, for example, the user A having made a clear expression of his or her intention. When the response from the user A has been sensed (YES in step S208), the processing proceeds to the next step S210.

When the response from the user A has not been sensed (NO in step S208), it is determined in step S209 whether or not a predetermined period of time has elapsed since the gesture was performed. When the predetermined period of time has not elapsed (NO in step S209), the processing returns to step S205 (or step S207). As a result, the robot 110R repeatedly performs the action to urge the user A to exercise for a predetermined period of time until the response from the user A is sensed. At this time, the robot 110R may increase stepwise the size of the gesture for urging the user A to exercise depending on the elapsed time or the number of repetitions, or may strengthen stepwise an expression of a message to be presented by the video audio output unit 110g depending on the elapsed time or the number of repetitions.

When the response from the user A has not been sensed (NO in step S208) and when the predetermined period of time has elapsed (YES in step S209), the processing proceeds to step S214. In this case, in step S214, the robot 110R transmits to the company B server 111 information that the task has not been achieved because the response from the user A cannot be sensed.

In step S210, it is determined whether the response from the user A is an affirmative response to the gesture of the robot 110R, or whether or not the response from the user A includes the expression of the intention to take exercise urged by the robot 110R. For example, if the response from the user A sensed in step S208 is a body action of the user A, the robot 110R may determine whether or not the body action of the user A includes the affirmative response or the expression of the intention to take exercise, by referring to a database that associates human behavior patterns with meanings indicated by the behavior patterns. For example, if the response from the user A sensed by the step S208 is a speech of the user A, the robot 110R may use voice recognition AI (not illustrated) to determine whether or not content of the speech of the user A includes the affirmative response or the expression of the intention to take exercise. When the response from the user A includes the affirmative response or the expression of the intention to take exercise (YES in step S210), the processing proceeds to step S211. When the response from the user A does not include them, or when the response from the user A includes a negative response (NO in step S210), the processing proceeds to step S214. In this case, in step S214, the robot 110R transmits to the company B server 111 information that the task has not been achieved because the affirmative response from the user A cannot be obtained.

In step S211, the robot 110R performs an action that corresponds to exercise of the user A. When the user A takes a walk or runs, the robot 110R walks or runs, accompanying the user A. For example, the robot 110R drives the actuators for the legs 110ea, 110eb, 110ec, and 110ed and accompanies the user A to move with the user A, while sensing the user A and the surroundings of the user A and the condition surrounding the robot 110R itself by using the RGB cameras 110ca and 110cd, the ranging sensors 110cb and 110ce, and the infrared cameras 110cc and 110cf as well as the microphones 110cg, 110ch, 110ci, and 110cj. The action of the robot 110R in step S211 is not limited to the body action of the robot 110R and may include, for example, an action to present a text or audio message using the video audio output unit 110g. In addition, a predetermined action in step S211 is not only an action for the user A while he or she is exercising, but also an action for the user A who is about to start exercising. For example, by moving to a direction away from the nearby area of the user A, the robot 110R may lead the user A, thereby causing the user A to start taking a walk. Note that in step S211, the robot 110R may perform a predetermined action in accordance with predetermined task content or may perform an action while mutually communicating with an external computer such as the company B server 111 or the smartphone 100. In the latter case, for example, while the user A is exercising, the robot 110R regularly or irregularly transmits data on the state of the user A to the external computer, and receives an action plan that is determined based thereon.

In step S212, the robot 110R determines whether or not the user A has finished exercising. For example, the robot 110R monitors the body motion of the user A using the RGB cameras 110ca and 110cd, and/or the infrared cameras 110cc and 110cf. When a state continues for a predetermined period of time in which the body action of the user A falls below the predetermined threshold, the robot 110R may determine that the user A has finished exercising. Alternatively, the robot 110R monitors the voice spoken by the user A using the microphones 110cg, 110ch, 110ci, and 110cj, and may determine that the user A has finished exercising when the robot 110R receives the expression of the intention communicating the end of exercise from the user A. If the robot 110R determines that the user A has finished exercising (YES in step S212), the processing proceeds to the next step S213. If the robot 110R determines that the user A continues exercising (NO in step S212), the processing returns to step S211 where the robot 110R performs the action that corresponds to the exercise of the user A.

In step S213, the robot 110R transmits to the company B server 111 the end notice indicating that the robot 110R finished performing the task. The end notice may include information on the exercise amount taken by the user A.

As described above, the robot 110R completes the series of processing from inducing the user A to exercise to reporting of the end of exercise of the user A.

FIG. 14 illustrates an example of an action performed by the robot according to the embodiment of the present disclosure. FIG. 14 depicts scene I to scene VI.

For example, scene I corresponds to step S201 in FIG. 13, scene II corresponds to step S206 in FIG. 13, scenes III and IV correspond to steps S207 to S209 in FIG. 13, scene V corresponds to steps S208 and S210 in FIG. 13, and scene VI corresponds to step S211 in FIG. 13.

Scene I represents a scene in which the user A who lacks exercise, a user B who is different from the user A, and the robot 110R used by the user A are at user A's home. At this time, the robot 110R waits at a location where a room can be easily overlooked or a location designated by the user A. In this example, it is assumed that the location where the robot 110R waits is outside of the nearby area (dotted line in FIG. 14) including the user A and his or her surroundings.

In Scene I, the calculation unit 110b of the robot 110R receives an exercise request for the user A from the company B server 111. This exercise request may be, for example, a request that is transmitted by the company A server 101 and transferred by the company B server 111, or a request that is newly generated by the company B server 111 based on the exercise request transmitted by the company A server 101.

Alternatively, the exercise request may be issued from an external computer capable of communicating with the robot 110R. For example, the exercise request may be transmitted from the company A server 101 to the robot 110R without going through the company B server 111, or may be transmitted to the robot 110R from an app of the company A or an app of the company B which is installed in the smartphone of the user A. Alternatively, the exercise request may be a request issued based on a result of sensing of the state of the user A, the sensing being done by a program that runs in the calculation unit 110b of the robot 110R, by using the sensor 110c.

Scene II represents a scene in which the robot 110R senses the position of the user A and autonomously moves to the nearby area of the user A based on the result thereof. Before moving, for example, the robot 110R may identify an activity in which the user A is engaged and determine the necessary urgency degree based on content of the identified activity.

Scene III is a scene in which the robot 110R performs an action to invite the user A to take a walk in the nearby area. In response to the received exercise request, the robot 110R uses the speakers 110ge and 110gf to output voice urging the user A to take a walk, or drives the movable unit 110e to make a gesture to invite the user A to take a walk. In this example, while walking on two legs, the robot 110R uses voice to make a gesture to face the user A and calls out "Let's go for a walk!". Note that the robot 110R may perform the action to induce to exercise after entering the nearby area or may enter the nearby area while performing the action to invite to exercise.

In this example, the robot 110R exhibits an action to behave as if the robot 110R itself has a desire to exercise. This can stimulate desire of the user A for altruistic behavior. The desire for altruistic behavior includes, for example, the desire to recognize the robot 110R as an individual and fulfill the desire of the robot 110R. However, the action performed by the robot 110R is not limited thereto. For example, the robot 110R may stimulate a self-actualization desire of the user A by communicating information on the user A to the user A. For example, in order to stimulate the desire of the user A that he or she continues to live in good health with a healthy body, the robot may perform an action to inform the condition that the user A lacks exercise or disadvantages of the lack of exercise. As an example of such an action, the robot 110R quietly approaches the user A while walking on all four legs and saying "You have only 1000 steps today. You had better take a walk.", and at the same time, performs a gesture to tap its feet on the spot.

Scene IV is a scene in which the robot continues to invite the user A to exercise more actively when no clear response from the user A can be sensed within the predetermined period of time since the robot 110R started to induce exercise. In this example, the robot 110R keeps telling the user A that the robot 110R wishes to go for a walk, by repeatedly outputting voice of "I want to go!" while moving around the user A.

Scene V is a scene in which the user A makes an affirmative or negative response and the robot senses the response. In this example, the user A stands up and makes a response, saying "Then, let's go." and communicating to the robot 110R the intention to go for a walk. The robot 110R senses a change in the posture and movement of the user A, as well as expression of the intention verbally or by gesture, with the sensor 110c. For example, by recognizing the user A from an image of the face or the whole body captured by the RGB camera 110ca and sensing the change in the posture (or bony framework) of the user A, the robot 110R recognizes the body action of the user A to determine whether or not a response from the user A is affirmative. Alternatively, the robot 110R, for example, determines from voice information picked up by the microphone 110cg whether or not the response from the user A is affirmative.

Scene VI is a scene in which the user A and the robot 110R leave home and start taking a walk. The robot 110R causes the user A to exercise according to the exercise request. The robot 110R reports an exercise state and an exercise result of the user A to an issuer of the exercise request.

Note that although taking a walk is described here as an example of exercise of the user A, the present disclosure is not limited thereto. The robot 110R may take the user A out for jogging, swimming, golf, tennis, or the like, or may cause the user A to take exercise using exercise equipment such as a room runner, a fitness bike, a dumbbell, or the like at home. For example, the robot 110R may select and suggest exercise to be recommended to the user A, according to the exercise history of the user A, presence or absence of the exercise equipment, weather at that time, or the like.

According to the present disclosure, it is possible to safely realize the demand or direct control of sensors or motor abilities held by devices of other companies. This makes it possible to perform some kind of action from cyber space to physical space through software by fusing the cyber space and the physical space, from the conventional distribution of information only in the cyber space, which can thus be expected as a basic technique for a wide variety of industrial uses.

What is claimed is:

1. A method for controlling a robot, comprising:
receiving, from a first computer that is external to the robot, instruction information that instructs the robot to encourage a user to exercise;
detecting a current position of the user through an optical sensor included in the robot;
controlling at least one pair of wheels or legs of the robot to cause the robot to move into a predetermined area including the current position of the user;
controlling at least one actuator included in the robot to cause the robot to perform a gesture for encouraging the user to exercise;
monitoring behavior of the user through the optical sensor or a microphone included in the robot; and
controlling, based on a result of the monitoring, the at least one actuator included in the robot to drive the robot along with exercise of the user,
wherein a second computer
transmits a message for encouraging the user to exercise, and
transmits, to the first computer via a network, request information that requests the robot to encourage the user to exercise, if it is determined that an amount of exercise taken by the user does not satisfy a predetermined target amount after transmission of the message, and
wherein the first computer
receives, from the second computer via the network, the request information, and
transmits the instruction information to the robot according to the request information.

2. The method according to claim 1, wherein
the driving of the robot along with the exercise of the user is performed if the behavior of the user includes an affirmative response to the gesture of the robot or expression of an intention to take exercise.

3. The method according to claim 1, wherein
the exercise of the user includes the user moving by walking or running, and
the driving of the robot along with the exercise of the user includes controlling the at least one pair of wheels or legs to cause the robot to move accompanying the user who is moving.

4. The method according to claim 3, wherein
the driving of the robot along with the exercise of the user further includes controlling the at least one pair of wheels or legs to cause the robot to encourage the user to start moving while leading the user in a direction away from the predetermined area.

5. The method according to claim 3, wherein
the gesture for encouraging the user to exercise is a gesture to convey to the user an intention of the robot to take a walk.

6. The method according to claim 1, wherein
the monitoring of the behavior of the user includes detecting a change in a posture of the user through the optical sensor.

7. The method according to claim 1, wherein
the monitoring of the behavior of the user includes acquiring voice information spoken by the user through the microphone and performing voice recognition on the voice information.

8. The method according to claim 1, wherein
the gesture for encouraging the user to exercise is repeatedly performed until a response from the user to the gesture is detected.

9. The method according to claim 1, further comprising:
before the robot starts to move into the predetermined area, detecting a remaining amount of a battery mounted in the robot; and
starting movement of the robot, if the remaining amount of the battery is larger than an amount of power required for driving the robot.

10. The method according to claim 1, further comprising:
monitoring the behavior of the user who is exercising through the optical sensor or the microphone; and
transmitting to the computer an end notice indicating the user has finished exercising, after determining that the user has finished exercising.

11. The method according to claim 1, further comprising:
transmitting, to the computer, necessary urgency degree information that indicates an urgency degree which is required for the computer to cause the robot to fulfill an instruction, wherein
the instruction information is transmitted from the computer to the robot if an urgency degree that should encourage the user to exercise meets the urgency degree which is required.

12. The method according to claim 1, wherein
the computer is a server or an information communication terminal that is communicable with the robot via a network.

13. The method according to claim 1, wherein
the detecting of the current position of the user includes:
- determining whether or not the user identified by the instruction information is detected around the robot; and
- acquiring information on the current position of the user in a three-dimensional space, if it is determined that the user is detected.

14. The method according to claim 1, wherein
the gesture for encouraging the user to exercise is a gesture involving an action of the robot to encourage the user.

15. The control method according to claim 1, wherein
the gesture is performed by driving the at least one pair of wheels or legs of the robot.

16. The control method according to claim 1, wherein
the exercise is walking or running, and
the driving of the robot along with the exercise of the user includes
- controlling the at least one pair of wheels or legs to induce the robot to take the user out of home, and
- controlling the at least one pair of wheels or legs to cause the robot to move accompanying the user who is walking or running out of home.

17. A robot comprising:
a main body;
the at least one pair of wheels or legs;
the at least one actuator;
at least one of the optical sensor or the microphone;
a processor; and
a memory that stores a program for causing the processor to execute the method according to claim 1.

18. A program which causes a processor mounted in a robot to perform the method according to claim 1.

19. A method for controlling a robot, comprising:
receiving, from a first computer that is external to the robot, instruction information that instructs the robot to encourage a user to exercise;
detecting a current position of the user through an optical sensor included in the robot;
controlling at least one pair of wheels or legs of the robot to cause the robot to move into a predetermined area including the current position of the user;
controlling at least one actuator included in the robot to cause the robot to perform a gesture for encouraging the user to exercise;
monitoring behavior of the user through the optical sensor or a microphone included in the robot; and
controlling, based on a result of the monitoring, the at least one actuator included in the robot to drive the robot along with exercise of the user,
wherein the detecting of the current position of the user includes
- determining whether or not the user identified by the instruction information is detected around the robot, and
- acquiring information on the current position of the user in a three-dimensional space, if it is determined that the user is detected.

* * * * *